(12) United States Patent
Nicolson et al.

(10) Patent No.: US 10,987,046 B2
(45) Date of Patent: *Apr. 27, 2021

(54) METHOD AND APPARATUS FOR EVALUATING CARDIAC FUNCTION

(71) Applicant: University of Leicester, Leicester (GB)

(72) Inventors: William Nicolson, Leicester (GB); G. Andre Ng, Leicester (GB)

(73) Assignee: University of Leicester, Leicester (GB)

( * ) Notice: Subject to any disclaimer, the term of this patent is extended or adjusted under 35 U.S.C. 154(b) by 150 days.

This patent is subject to a terminal disclaimer.

(21) Appl. No.: 15/880,804

(22) Filed: Jan. 26, 2018

(65) Prior Publication Data

US 2018/0160927 A1 Jun. 14, 2018

Related U.S. Application Data

(63) Continuation of application No. 13/635,709, filed as application No. PCT/GB2011/050533 on Mar. 17, 2011, now Pat. No. 9,913,592.

(30) Foreign Application Priority Data

Mar. 22, 2010 (GB) ..................................... 1004743

(51) Int. Cl.
*A61B 5/0468* (2006.01)
*A61B 5/361* (2021.01)
(Continued)

(52) U.S. Cl.
CPC .............. *A61B 5/361* (2021.01); *A61B 5/316* (2021.01); *A61B 5/349* (2021.01); *A61B 5/363* (2021.01); *A61B 5/364* (2021.01)

(58) Field of Classification Search
CPC . A61B 5/02028; A61B 5/024; A61B 5/20405; A61B 5/04012; A61B 5/0452;
(Continued)

(56) References Cited

U.S. PATENT DOCUMENTS

2004/0015088 A1 1/2004 Gray et al.
2004/0220640 A1 11/2004 Burnes et al.
(Continued)

FOREIGN PATENT DOCUMENTS

WO WO-03057033 A1 7/2003
WO WO-2005074566 A2 8/2005

OTHER PUBLICATIONS

Nicolson, William B et al. "A novel surface electrocardiogram-based marker of ventricular arrhythmia risk in patients with ischemic cardiomyopathy." Journal of the American Heart Association vol. 1,4 (2012): e001552. doi: 10.1161/JAHA.112.001552.*
(Continued)

*Primary Examiner* — Eugene T Wu
(74) *Attorney, Agent, or Firm* — Winstead PC

(57) ABSTRACT

A method for assessing the electrical function of a heart that includes: (1) for each of a plurality of leads of an ECG, determining a value derived from the output of that lead and which corresponds to an action potential duration; (2) for each of the plurality of leads of the ECG, determining a value derived from the output of that lead and which corresponds to a diastolic interval; (3) for each of the plurality of leads of the ECG, determining a relationship between the determined values for action potential duration and for diastolic interval; and (4) assessing the differences between the determined relationships for each of the plurality of leads. The invention further relates to apparatus and a computer program that may be used in the method.

17 Claims, 18 Drawing Sheets

(51) Int. Cl.
  A61B 5/316 (2021.01)
  A61B 5/349 (2021.01)
  A61B 5/363 (2021.01)
  A61B 5/364 (2021.01)
(58) Field of Classification Search
  CPC ..... A61B 5/046; A61B 5/0464; A61B 5/0468; A61B 5/7235; A61B 5/7264; A61B 5/7275
  See application file for complete search history.

(56) References Cited

U.S. PATENT DOCUMENTS

2007/0244401 A1   10/2007   Xue et al.
2017/0112402 A1   4/2017   Nicolson et al.

OTHER PUBLICATIONS

Yue et al. "Global Endocardial Electrical Restitution in Human Right and Left Ventricles Determined by Noncontact Mapping". Journal of the American College of Cardiology. vol. 46, Issue 6, Sep. 20, 2005, pp. 1067-1075.*

H. M. Dobrovolny, C. M. Berger, N. H. Brown, W. K. Neu and D. J. Gauthier, "Spatial heterogeneity of restitution properties and the onset of alternans," 2009 Annual International Conference of the IEEE Engineering in Medicine and Biology Society, Minneapolis, MN, 2009, pp. 4186-4189. doi: 10.1109/IEMBS.2009.53339.*

Martelli, Luca, "International Search Report" for PCT/GB2011/050533, dated Aug. 9, 2011, 3 pages.

Malik, Marek, "Measurement, interpretation and clinical potential of QT dispersion", J.Am. Coll. Cardiol, vol. 36, No. 6, 2000, 1749-1766.

Hampton, J. R., "The ECG Made Easy", 7th Edition, Churchill Livingstone, 1997.

Narayan, Sanjiv M., et al., "T-Wave Alternans, Restitution of Human Action Potential Duration, and Outcome," J. Am. Coll. Cardiol., vol. 50, No. 25, 2007; 10 pages.

Nicolson, Willliam B., et al. "A Novel Surface Electrocardiogram-Based Marker of Ventricular Arrhythmia Risk in Patients With Ischemic Cardiomyopathy," J. Am. Heart Assoc. 2012, pp. 1-10.

Wikipedia. "Mean squared error". <http://en.wikipedia.org/wiki/Normalization_(statistics)>. Feb 11, 2010 via Wayback machine.

Wikipedia. "Normalization (statistics)". <http://en.wikipedia.org/wiki/Normalization_(statistics)>. Feb 24, 2010 via Wayback machine.

Nash et al. "Whole heart action potential duration restitution properties in cardiac patients: a combined clinical and modelling study". Experimental Physiology, vol. 91, Issue 2, pp. 339-354. Mar. 2006.

Yue et al. "Global Endocardial Electrical Restitution in Human Right and Left Ventricles Determined by Non contact Mapping". Journal of American College of Cardiology, vol. 46, Issue 6, pp. 1067-1075. Sep. 20, 2005.

Dobrovolny et al. "Spatial heterogeneity of restitution properties and the onset of alternans". Engineering in Medicine and Biology Society, 2009. EMBC 2009. Annual International Conference of the IEEE.

Nicolson et al. "Pilot Study exploring the regional repolarisation instability index in relation to myocardial heterogeneity and prediction of ventricular arrhythmia and death". BCS abstracts, Heart, vol. 97, Suppl 1. Jun. 2011.

Watanabe T., et al. "Regional prolongation of ARI and altered restitution properties cause ventricular arrhythmia in heart failure." American Journal of Physiology—Heart and Circulatory Physiology Jan. 2002, 282 (1) H212-H218.

Fuller M., et al. "Estimates of Repolarization Dispersion From Electrocardiographic Measurements." Circulation. 2000;1 02:685-691, doi:1 0.1161/01.CIR.1 02.6.685.

Pueyo, E., et al. "Cardiac repolarization analysis using the surface electrocardiogram." Philosophical Transactions of the Royal Society of London A: Mathematical, Physical and Engineering Sciences 2009 367 213-233; DOI: 10.1 098/rsta.2008.0230. Published Jan. 28, 2009.

Clayton, R., Taggart, P. "Regional differences in APD restitution can initiate wavebreak and re-entry in cardiac tissue: A computational study." Biomed Eng Online. 2005; 4: 54. Published online Sep 20, 2005.

Fossa, A. QT prolongation modifies dynamic restitution and hysteresis of the beat-to-beat QT-TQ interval relationship during normal sinus rhythm under varying states of repolarization. J Pharmacal Exp Ther. Feb. 2006;316(2):498-506. Epub Oct. 4, 2005.

Fossa, A. Analyses of dynamic beat-to-beat QT-TQ interval (ECG restitution) changes in humans under normal sinus rhythm and prior to an event of torsades de pointes during QT prolongation caused by sotalol. Ann Noninvasive Electrocardiol. Oct. 2007;12(4):338-48.

* cited by examiner

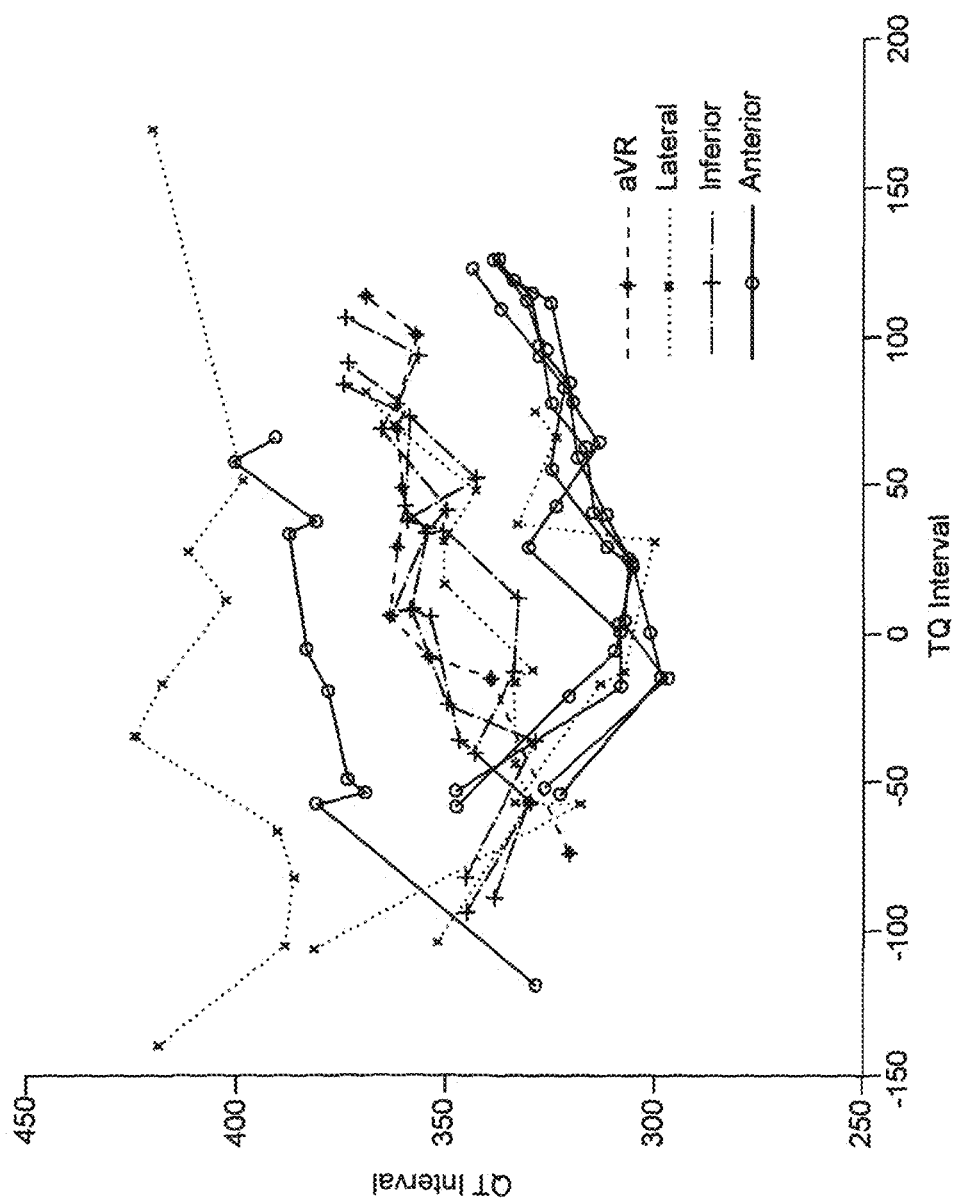

METHOD AND APPARATUS FOR EVALUATING CARDIAC FUNCTION

This application is a continuation of U.S. patent application Ser. No. 13/635,709, which entered the national-stage in the U.S. under 35 U.S.C. § 371 on Sep. 18, 2012. U.S. patent application Ser. No. 13/635,709 is a national-stage application of PCT/GB2011/050533, which has an international filing date of Mar. 17, 2011. PCT/GB2011/050533 claims priority to GB 1004743.9, filed on Mar. 22, 2010. U.S. patent application Ser. No. 13/635,709, PCT/GB2011/05053, and GB 1004743.9 are each incorporated herein by reference.

The present invention relates to a method for evaluating cardiac function, in particular a method that utilises the information provided by electrocardiography. The invention also relates to an apparatus in which the aforementioned method may be practised, including a computer program.

The intrinsic conducting system of the heart permits electrical impulses originating from the sinoatrial node to travel through the cardiac tissue in a controlled manner. The passage of this electrical impulse through the heart tissue produces a wave of contraction through the cardiac tissue. The wave of contraction is followed by a period of relative electrical calm in the heart tissue, which corresponds to relaxation of the cardiac tissue. Arrhythmias occur when this normal, organised electrical activity of the heart becomes disrupted. Worldwide 3 million people a year die from sudden cardiac death. In most cases there is no warning and the heart is stopped by a sudden arrhythmia. Some people are at high risk of sudden cardiac death, but this can be prevented by an implantable cardioverter defibrillator, which is implanted in a minor operation.

In the UK, subjects are screened for risk of sudden cardiac death using the National Institute for Health and Clinical Excellence (NICE) guidelines (a screening that is based on a mixture of physiological and electrophysiological measurements and an understanding of the subject's clinical history). However, most of the people who die from sudden cardiac death are not identified by these guidelines.

Assessment of the health of the heart by measuring its electrical activity is known. For example, one can measure the electrical activity of the heart with the use of intra-cardiac electrodes that are directly applied to the cardiac tissue.

This is however a particularly invasive technique that is not preferable for the routine assessment of subjects and that has not been clearly shown to demonstrate any clinical relevance for assessing cardiac function such as the risk of arrhythmia. Electrocardiography (ECG) has been developed as a non-invasive procedure for studying the electrical activity of the heart. ECG involves the placing of a plurality of electrodes on the skin surface of a subject. An understanding of the electrical activity of the heart may be identified from the potential difference (i.e. leads) between combinations of the plurality of electrodes. Conventionally, a collective assessment of ECG leads provide a classic ECG tracing, which comprises a P wave, a QRS complex and a T wave, and which demonstrate periods of electrical activity that vary from the isoelectric line. It has been suggested that ECGs may be useful for identifying arrhythmia of the heart by measuring the dispersion of QT durations on an ECG tracing. Measuring changes in this QT duration as an indicator of cardiac arrhythmia has however since been discredited; to the degree that the cardiology community no longer view the QT dispersion assessment as a clinically relevant way to establish arrhythmia risk (see, for example, Malik et al.; JACC; 2000; 36:1749-66).

Consequently, there remains a need for further methods and apparatus capable of identifying the risk of sudden cardiac death due to arrhythmia. Such methods and apparatus would be particularly useful for identifying those individuals who are most likely to benefit from the implantation of an implantable cardioverter defibrillator or from treatment with anti-arrhythmic therapeutics.

It has surprisingly been found that the relationship between action potential duration and the diastolic interval, as measured by the leads of an ECG, presents a considerable inter-lead variation in those individuals who go on to develop an arrhythmia when compared to the same results for patients with no arrhythmia.

Accordingly, in the first aspect of the present invention, there is provided a method for assessing the electrical function of a heart, comprising the steps of:—
  a. for each of a plurality of leads of an ECG, determining a value derived from the output of that lead and which corresponds to an action potential duration;
  b. for each of the plurality of leads of the ECG, determining a value derived from the output of that lead and which corresponds to a diastolic interval;
  c. for each of the plurality of leads of the ECG, determining a relationship between the determined values for action potential duration and for diastolic interval;
  d. assessing the differences between the determined relationships for each of the plurality of leads.

An ECG provides a cutaneous electrocardiagraphic measurement of the electrical functioning of the heart. As would be known to the skilled person, an ECG includes a plurality of electrodes that are placed on specific external positions of the body. A lead of an ECG is the potential difference between two or more of these electrodes. Consequently, a lead provides an electrical output that corresponds to a changing potential difference between the electrodes that form the lead.

The plurality of leads available in an ECG would be known to the skilled person (see, for example, "The ECG made easy", 4th edition, John R. Hampton, Churchill Livingstone, 1997). For example, the leads may comprise or consist: limb leads, chest leads, posterior leads, anterior leads, lateral leads, inferior leads, or any combination thereof. For example, the limb leads may comprise or consist: right arm (Red), left arm (Yellow), left leg (Green), right leg (Black), or any combination thereof. For example, the chest leads may comprise or consist: V1 (right sternal edge, 4th intercostal space), V2 (left sternal edge, 4th intercostal space), V3 (halfway between V2 and V4), V4 (position of the apex beat—e.g. intersection of the 5th intercostal space and mid-clavicular line), V5 (anterior axillary line), V6 (mid-axillary line), or any combination thereof. For example, the posterior leads may comprise or consist of V7 (left posterior axillary line, straight line from V6), V8 (left midscapular line, straight line from V7) and V9 (left paraspinal line, straight line from V8). For example, the anterior leads may comprise or consist: V1, V2, V3, V4, or any combination thereof. For example, the lateral leads may comprise or consist: V5, V6, I, aVL, or any combination thereof. For example, the inferior leads may comprise or consist: II, III, aVF, or any combination thereof.

The number of leads used in the method according to the present invention must exceed 2, and may be 5 or more, 10 or more, or 12 or more. Optionally, the number of leads do not exceed 4096. The plurality of leads of the present method may be 5, 12 or 256 lead configurations.

The action potential duration is the period of myocyte electrical activity, which would be understood to consist of the initial depolarisation, a plateau phase and finally repolarisation phase. The diastolic interval is the interval between action potentials, when the myocyte is electrically quiescent. The output from each lead of an ECG provides sufficient information concerning the electrical activity of the heart for a skilled person to derive therefrom a value for both the action potential duration and the diastolic interval. For example, the output of ECG leads may be converted into an ECG tracing, e.g. comprises a P wave, a QRS complex and a T wave. The skilled person would have no difficulty in preselecting the relevant portion of the ECG tracing that corresponds to the action potential duration and to the diastolic interval. By measurement of the duration of these preselected portions one can determine a value from the output of the lead and which corresponds to the action potential duration and to the diastolic interval.

The preselected portion that corresponds to the action potential duration can, for example, be the QT or the JT interval. The preselected portion that corresponds to the diastolic interval can, for example, be the TQ interval. The process of determining the value for each lead in step a. should be consistent. The process of determining the value for each lead in step b. should be consistent.

It should be understood that how one precisely calculates the beginning and end of each of these intervals (in order to identify their duration) is of less significance than the fact that the value for the JT, QT and TQ intervals is measured for each in the methods of the present invention in a consistent manner. For example, the QT interval may be measured:—from the beginning of the QRS complex to the end of the T wave; from the onset of the R wave to the end of the T wave; from the beginning of the QRS complex to the peak of the T wave, or; from the onset of the R wave to the peak of the T wave. For example, the JT interval may be measured:—from the point of separation between the QRS complex and the end of the T wave, or; from the point of separation between the QRS complex and the peak of the T wave. For example, the TQ interval may be measured:—from the end of the T wave to the beginning of the QRS complex; from the end of the T wave to the onset of the R wave; from the peak of the T wave to the beginning of the QRS complex, or; from the peak of the T wave to the onset of the R wave. (see, for example, Malik et al.; JACC; 2000; 36:1749-66)

Steps a. and b. may be repeated a plurality of times for example 2-2000, 2-1000, 2-100, 5-50, 10-40 or 10-20 in order to determine the values for the duration of a number of action potentials and the duration of a number of diastolic intervals for each lead. The relationship determined in step C. may therefore be a dynamic relationship (i.e. a relationship that can be described by a curve plotted on a graph of duration of action potential against duration of diastolic interval).

The relationship between the action potential duration and the diastolic interval may be determined in a number of ways that would be apparent to the skilled person. For example, the relationship between a single action potential duration and a single diastolic interval may be determined as a ratio of the two. When a number of action potential durations and diastolic intervals are determined for each lead, the relationship can be determined numerically (i.e. by formulae) or graphically (i.e. by plotting a graph of action potential duration against diastolic interval, or vice versa). The determining of the relationship in step c. should be consistent.

In one embodiment of the present invention, determining the relationship in step c. may comprise establishing for each repetition of step a. and b. the relationship between the determined values for action potential and the determined values for diastolic interval for each of the plurality of leads.

Such a relationship may be plotted on a graph of action potential duration against diastolic interval duration.

There are many ways in which the difference between the relationships identified in step c. may be assessed in step d. For example, the relationship between a single action potential duration and a single diastolic interval may be determined as a ratio of the two for each lead, the difference between the ratios for each lead may be assessed numerically. For example, when a number of action potential durations and diastolic intervals are determined for each lead, the differences between the determined relationships may be assessed by identifying or quantifying the difference in the gradient or gradients of the curves established by plotting the values for action potential duration against diastolic interval (or vice versa) for each lead on a graph. This difference may be visually apparent from degree of separation of the curves for each lead over the length of the curves, or by changes in the degree of separation of the curves for each lead over the length of the curves.

Numerical analysis of the curves may also be used to quantify the differences. For example, the following process may be applied:—(1) application of logistic regression to the data set to derive a polynomial equation, (2) application of this polynomial equation, adjusting the linear constant to achieve best fit, to each lead in turn, (3) using logistic regression to calculate the residuals this technique produces for each lead, (4) Summing the residuals will produce a measure of the differences between the relationships. At point (1) a spline could be used in place of the polynomial equation. At point (1) linear regression could be used separately on groups of leads from each cardiac region, the resulting equations could then be applied to the leads from their corresponding regions as described in steps (2), (3) and (4). In a further example, the following process may be applied:—(1) the standard deviation of the action potential difference from all leads is calculated for each determined diastolic interval length, (2) the mean of this value is taken as a marker of heterogeneity of the data In one embodiment of the present invention, assessing the difference in step d. may comprise, for each repetition of step a. and b.:—
  (i) establishing the mean point between the relationships determined in step c. for each of the plurality of leads,
  (ii) for each lead, calculating the square of the residual from the mean point to the relationship determined for that lead (e.g. the square of the variation from the mean);
Assessing the difference in step d. may further comprise:—
  (iii) for each lead, calculating the mean value of the square of the residuals calculated in step (ii) for each repetition of step a. and b.
Assessing the difference in step d. may further comprise:—
  (iv) calculating the normalised mean value by dividing the mean value calculated in step (iii) by the same mean value when calculated from the assessment of subjects at normal risk of developing cardiac arrhythmia, or by the mean of the values of step (iii) for all of the plurality of leads.

Assessing the difference in step d, may further comprise:—

(v) identifying the largest normalised mean value calculated in step (iv) out of the normalised mean values calculated for each of the plurality of leads.

The values calculated in step (v) have been designated the Regional Repolarisation Instability Index (R212). The method may be applied separately to the anterior, inferior and/or lateral leads. aVR may be omitted.

It has been found that the greater the difference between the relationships identified for each lead (which can be demonstrated by a relatively large R212), the greater the risk that the heart being assessed will develop a cardiac arrhythmia. Thus, the method of the present invention, when applied to the outputs derived from an ECG applied to a subject, may be used as in a method of prognosis to assess the risk of the subject developing arrhythmia. Essentially, therefore, an increased level of heterogeneity between the relationships determined for each lead (which can be demonstrated by a relatively large R212) results in an increased risk of cardiac arrhythmia.

An assessment of the risk of developing cardiac arrhythmia derived from anatomical imaging modalities such as a cardiac magnetic resonance scans may be combined with the methods of the present invention.

Consequently, in one embodiment of the present invention, steps a. to d. may be carried out on the output derived from an ECG applied to a subject to be examined for the risk of developing cardiac arrhythmia. The method may further comprise the carrying out of the steps a. to d. on the output derived from an ECG applied to a subject that has been determined to have normal risk of developing cardiac arrhythmia, and comparing the differences in step d. assessed for the output from the subject to be examined with the differences in step d. assessed for the output from the subject determined to be at normal risk of developing cardiac arrhythmia (or a predetermined value that corresponds to the differences in step d. assessed for the output from subjects determined to be at normal risk of developing cardiac arrhythmia). When the differences are determined to be greater for the subject to be examined than those of the subject determined to be at normal risk (or than the predetermined value), the subject to be examined is at increased risk of developing a cardiac arrhythmia (increased, being at greater risk than normal or vice versa).

The predetermined value is derived from the assessment of subjects determined to be at normal risk of developing cardiac arrhythmia (i.e. the mean value for a group of normal subjects). Normal subjects therefore represent a control group. Determining whether or not an individual subject is normal with respect to their risk of cardiac arrhythmia is a clinical question well within the abilities of the skilled person. However, in the interests of clarity, but not wishing to be restricted further, individuals in such a group will be characterised by structurally normal heart, as determined by echocardiography, and no history of palpitation, syncope or other cardiac problems. Optionally a normal subject has no family history of cardiac death.

In a further embodiment of the present invention, instead of the further step of carrying out of the steps a. to d. on the output derived from a subject that has been determined to have normal risk of developing cardiac arrhythmia (or a related predetermined value), there may be a further step of carrying out of the steps a. to d. on the output derived from a subject that has been determined to have increased risk of developing cardiac arrhythmia (or a related predetermined value, e.g. a value provided from subjects known to have had cardiac arrhythmia). When the differences are determined to be equal or greater for the subject to be examined than those of the subject determined to have increase risk (or a related predetermined value), the subject to be examined is at increased risk of developing a cardiac arrhythmia.

In yet a further embodiment of the present invention, steps a. to d. may be carried out on the output derived from an ECG applied to a subject to be examined for the risk of developing cardiac arrhythmia at a first time point. The method may further comprise the carrying out of the steps a. to d. on the output derived from an ECG applied to the same subject at one or more later time point, and comparing the differences in step d. assessed for the output from the subject to be examined at a first time point with differences in step d. assessed for the output from the subject at one or more later time point. Such a method may be used to monitor the progression of heart disease associate with cardiac arrhythmia. A therapeutic agent may be administered to the subject after the first time point, but before the one or more later time point. Such a method may be capable of determining if the therapeutic agent has the ability to treat cardiac arrhythmia. The therapeutic agent may be any anti-arrhythmic agent, or proposed anti-arrhythmic agent (ie amiodarone).

In one embodiment of the present invention, the method is practiced on the output derived from the electrical activity of a heart beating under its own direction. Optionally the pace of the heart may controlled during or prior to the method by exercise or by the administration of a therapeutic agent capable of controlling heart rate.

In an alternative embodiment, the output is derived from the electrical activity of a heart stimulated by external electrical provocation. In such embodiments a pacing spike (e.g. ventricular pacing spike) can be identified on the ECG tracing that corresponds to the external electrical provocation. A plurality of such pacing spikes (collectively termed a drive train) may be repeated prior to determining the value of the action potential duration and the diastolic interval from the output. The drive train may include 1-100, 1-20, 1-15, 1-10, 1-8, 8-10 or 8-100 pacing spikes. In embodiments where steps a. and b. are repeated, a drive train may be included prior to each repetition.

In methods of the present invention in which pacing spikes are used, the QT interval may be measured:—from the pacing spike to the end of the T wave, or; from the pacing spike to the peak of the T wave. The TQ interval may be measured:—from the end of the T wave to the start of the pacing spike or from the peak of the T wave to the start of the pacing spike. Pacing spikes may be repeatedly applied. Results obtained from repeated cycles of provocation may be combined for analysis of the required interval lengths. For example, a combined image of the T waves may be established and from this the T wave axis identified. This axis is then used to determine the peak of the T wave. From this the end of the T wave is determined as the intercept of two lines, the first is based on the T wave peak and the steepest T wave gradient and second is based on the baseline.

In one embodiment a preselected number of T waves may be measured as part of the method of the present invention, for example the method may include 8 to 10 repetitions of electrical provocation before a measurement of T wave is established. Measuring to the end of the T wave may be achieved in a similar manner.

When the output is derived from the electrical activity of a heart stimulated by multiple external electrical provocations, steps a. and b. may be repeated a plurality of times corresponding to the number of external electrical provocations in order to determine the values for the duration of a number of action potentials and the duration of a number of diastolic intervals for each lead following each external electrical provocation. In some embodiments action potential durations and diastolic intervals are only measured after a first pre-determined number of provocations (e.g. 8 to 10 provocations). In some embodiments, the duration between the external electrical provocations are maintained constant or reduced over time. Where the provocations are maintained constant it can be observed that the QT and other intervals progressively change. This concept is termed QT adaptation and may be analysed with the data in the attached graphs when considering arrhythmia risk. (As part of the present inventions, increased change corresponds to increased risk of developing cardiac arrhythmia).

External electrical provocation can be by direct application of electrical provocation to the cardiac tissue (e.g. by an electrophysiological catheter), or by the application of an electrical provocation applied to the skin of the subject.

In another embodiment it is noted that a false impression of the dispersion of the QT intervals can be given by inappropriate measurement of leads that for example have an insufficiently distinct T wave or display marked change in T wave morphology as the action potential duration shortens. Criteria for censoring such T waves (i.e. omitting such T waves from analysis are contemplated as part of the present invention.

In a second aspect of the present invention there is provided a method for determining a subject's need for the implantation of an implantable cardioverter defibrillator or the need for administration of an anti-arrhythmic agent, comprising the steps of:—
a. for each of a plurality of leads of an ECG directed to the subject, determining a value derived from the output of that lead and which corresponds to an action potential duration;
b. for each of the plurality of leads of the ECG directed to the subject, determining a value derived from the output of that lead and which corresponds to a diastolic interval;
c. for each of the plurality of leads of the ECG directed to the subject, determining a relationship between the determined values for action potential duration and for diastolic interval;
d. assessing the subjects need for the implantation of an implantable cardioverter defibrillator or need for the administration of an anti-arrhythmic agent based on the assessment of the differences between the determined relationships for each of the plurality of leads.

Such a method can be used in a method of treating a subject with cardiac arrhythmia and further comprises the step of administering an effective amount of one or more anti-arrhythmic agent to a subject if the subject is assessed by step d. to require such treatment.

Any clinically relevant anti-arrhythmic agent may be used, for example amiodarone.

All optional features of the first aspect of the present invention maybe included in the second aspect of the present invention. For the avoidance of doubt, it should be understood that when the method identifies that the subject is at increased risk of developing cardiac arrhythmia, there is an increased need for the implantation of an implantable cardioverter defibrillator in the subject or the administration of an anti-arrhythmic agent to the subject (e.g. compared to an individual at normal risk of developing cardiac arrhythmia).

In a third aspect of the present invention there is provided apparatus for assessing the function of the heart, comprising a computer arranged to receive input from each of a plurality of leads of an ECG and arranged to:—
a. for each of a plurality of leads of the ECG, determine a value derived from the output of that lead and which corresponds to an action potential duration;
b. for each of the plurality of leads of the ECG, determine a value derived from the output of that lead and which corresponds to a diastolic interval;
c. for each of the plurality of leads of the ECG, determine a relationship between the determined values for action potential duration and for diastolic interval;
d. assess the differences between the determined relationships for each of the plurality of leads.

The apparatus according to the third aspect of the present invention is arranged so as to be capable of operating the methods according to the earlier aspects of the present invention. Consequently, all features of the first and second aspects of the present invention maybe included in the third aspect of the present invention. For example:—

The apparatus may include an ECG device. The ECG device may include a plurality of electrodes configured to provide any of the lead combinations described for the first aspect of the present invention.

The output from each lead of an ECG provides sufficient information concerning the electrical activity of the heart for the computer to derive therefrom a value for both the action potential duration and the diastolic interval. For example, the computer may be configured to convert the output of ECG leads into an ECG tracing, e.g. comprises a P wave, a QRS complex and a T wave. The computer may be configured to preselect the relevant portion of the ECG tracing that corresponds to the action potential duration and to the diastolic interval. Appropriate pre-selection criteria are discussed above with respect to the first aspect of the present invention.

Steps a. and b. may be repeated a plurality of times in order to determine the values for the duration of a number of action potentials and the duration of a number of diastolic intervals for each lead.

The computer may be arranged to determine the relationship between the action potential duration and the diastolic interval in a number of ways, see for example the determination discussed in the first aspect of the present invention The computer may be arranged to assess the difference between the relationships identified in step c. may, see for example the determination discussed in the first aspect of the present invention.

The apparatus of the present invention, when applied to the outputs derived from an ECG applied to a subject, may be used in a method of prognoses of the risk of that subject developing cardiac arrhythmia.

The apparatus may further comprise an electrophysiological catheter capable of providing an electrical provocation to the cardiac tissue.

The apparatus may further comprise a computer program product that when run on the computer causes it to be configured in the aforementioned manners.

In a fourth aspect of the present invention, there is provided a computer program product when run on a computer arranged to receive input from each of a plurality of leads of an ECG causes the computer to:—
a. for each of a plurality of leads of the ECG, determine a value derived from the output of that lead and which corresponds to an action potential duration;
b. for each of the plurality of leads of the ECG, determine a value derived from the output of that lead and which corresponds to a diastolic interval;

c. for each of the plurality of leads of the ECG, determine a relationship between the determined values for action potential duration and for diastolic interval;

d. assess the differences between the determined relationships for each of the plurality of leads.

The computer program according to the fourth aspect of the present invention may be included in the apparatus of the third aspect of the present invention. Consequently, all features of the previous aspects of the present invention maybe included in the fourth aspect of the present invention.

In yet a further aspect of the present invention, there is provided a method as substantially hereinbefore described and with reference to the figures.

In yet a further aspect of the present invention, there is provided apparatus as substantially hereinbefore described and with reference to the figures.

In yet a further aspect of the present invention, there is provided a computer program as substantially hereinbefore described and with reference to the figures.

The present invention will now be described, by way of example, with reference to accompanying figures, in which:—

FIG. 2a shows a continuous cutaneous APD restitution graph from a subject suffering from arrhythmia.

Figure 5:
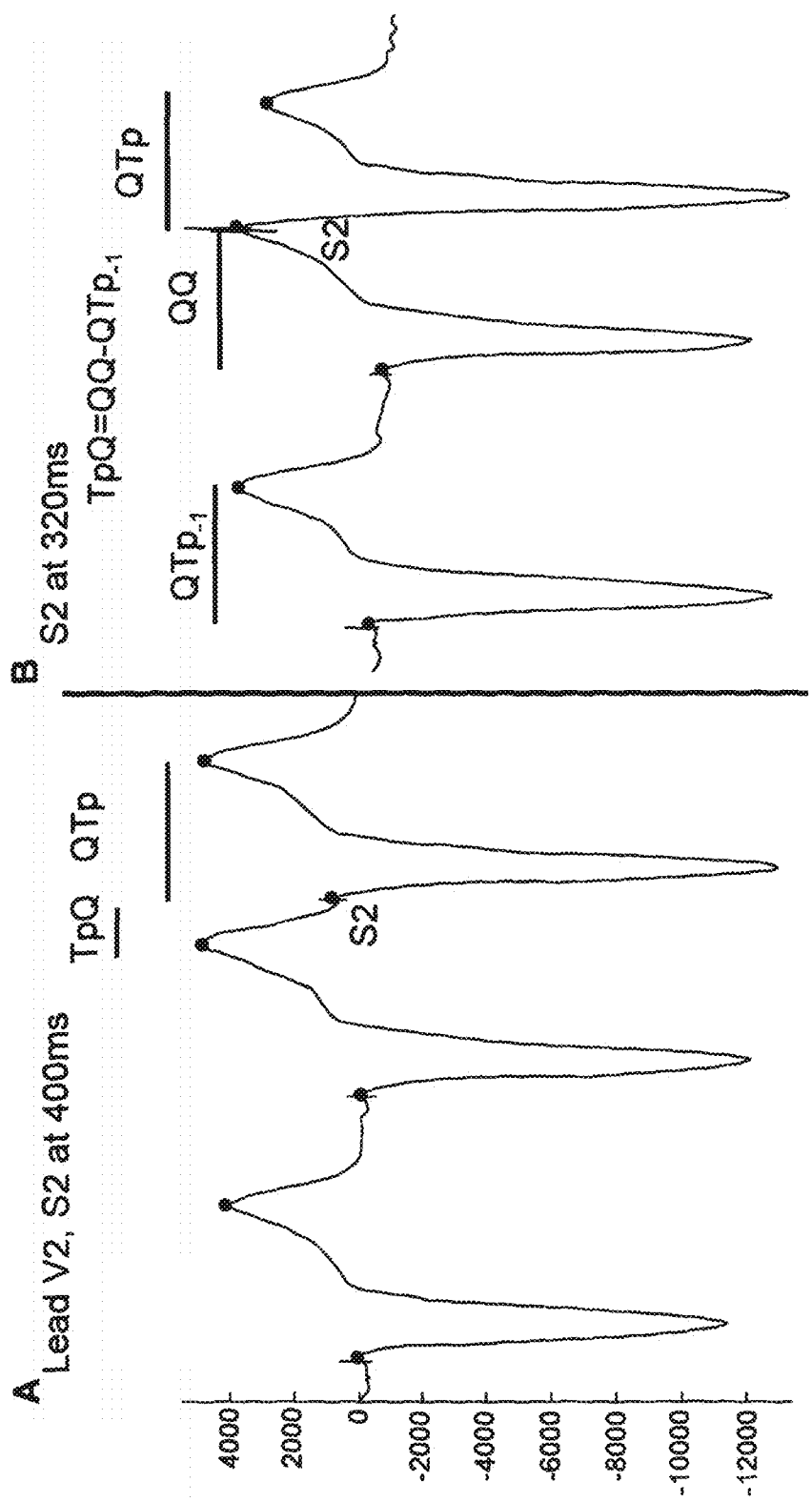

FIG. 5 shows the technique by which TpQ and QTp measurements are made: when an S2 arrives after the T wave peak the TpQ and QTp are measured as shown on the left of the diagram. However, if the S2 occurs before the T wave peak the TpQ is effectively negative. In this case it is measured by subtracting the QTp1 interval (QTp for drive cycle beat) from the QTp2, in the example above this would give a TpQ close to zero.

Figure 6:
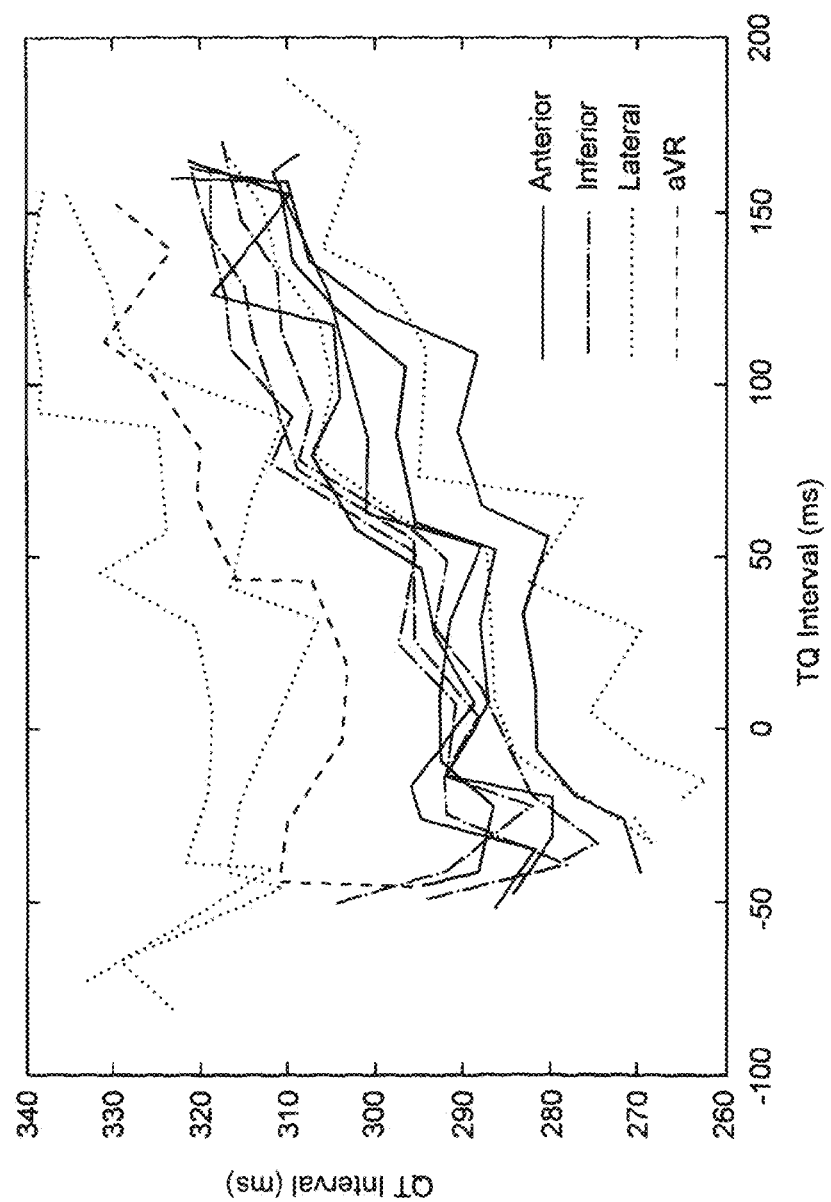

FIG. 6 is a graph that illustrates the dynamic relationship between QTp interval and TpQ interval for 12 leads, marked to show the 4 lateral leads, 3 inferior leads, 4 anterior leads and 1 aVR lead. Results for population mean values of all patients in the study shown on the graph.

Figure 7:
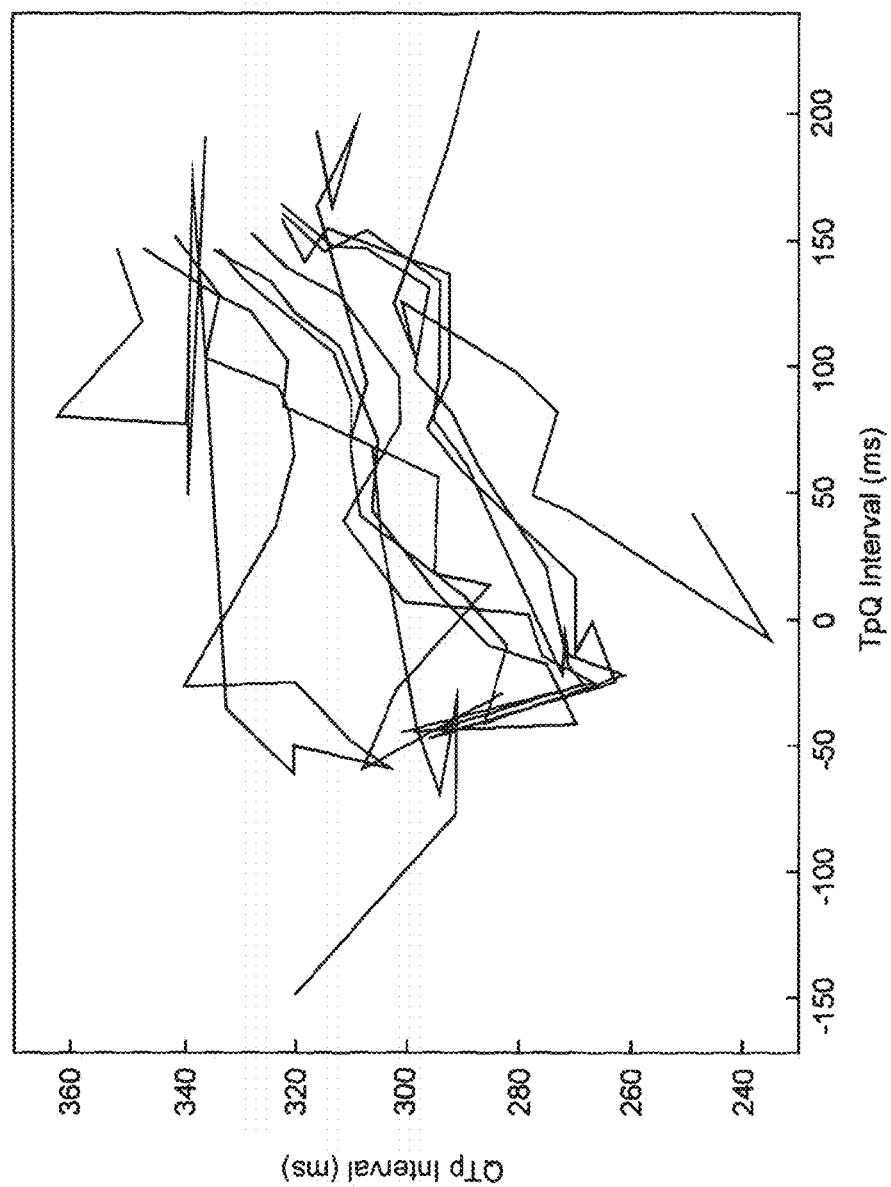

FIG. 7 is a graph that illustrates the dynamic relationship between QTp interval and TpQ interval for 12 leads prepared for the assessment of R212 of a single patient.

Figure 8:
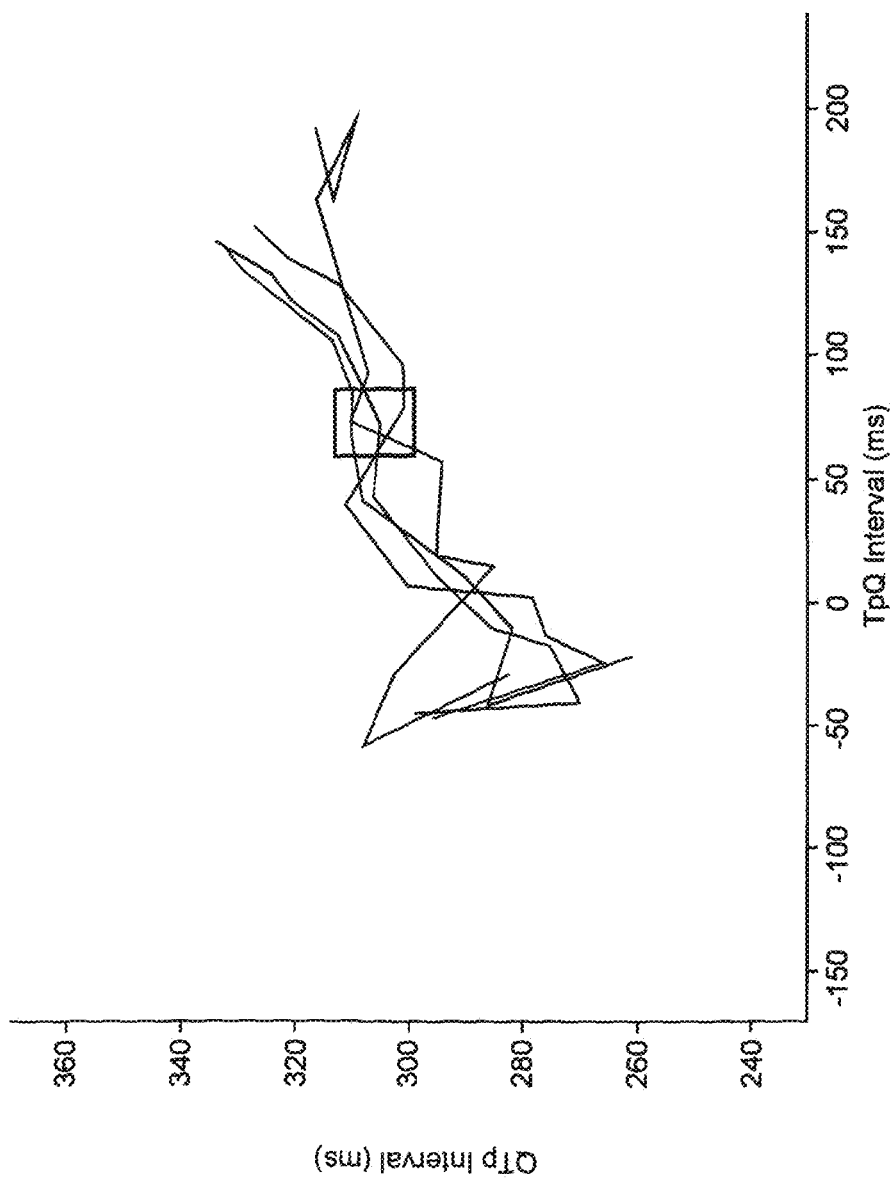

FIG. 8 provides a selection of only the anterior leads of the graph of FIG. 7, prepared for the assessment of R212.

Figure 9:
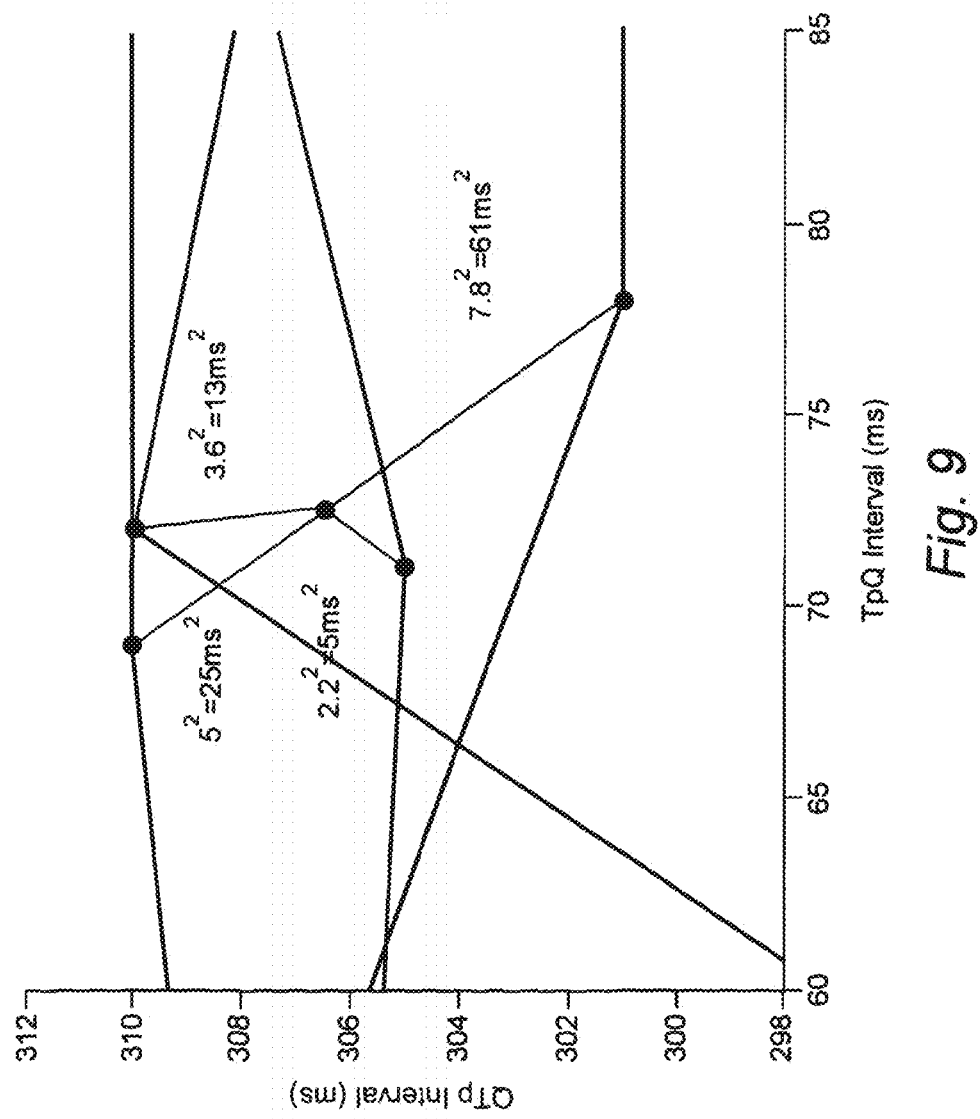
Figure 10:
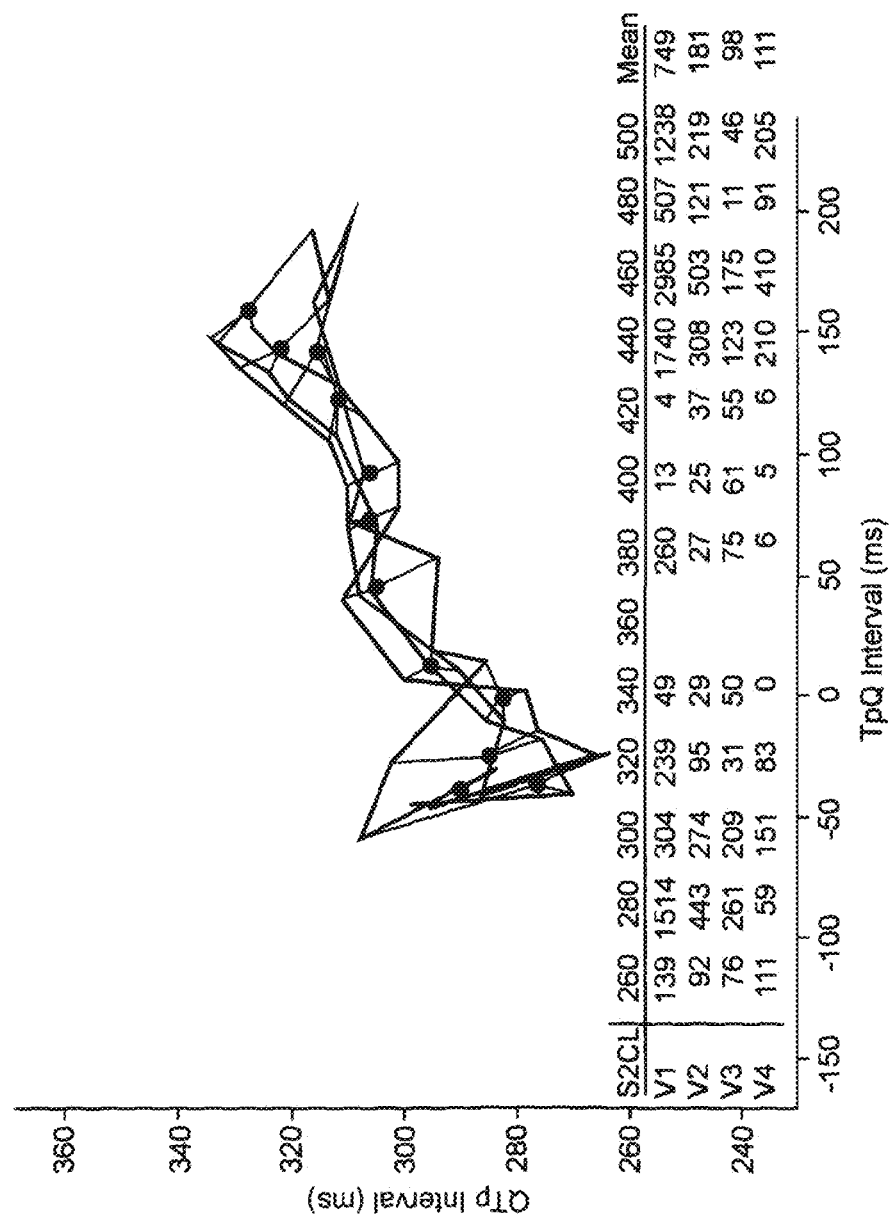

FIG. 9 provides a blown up image of the box provided in the graph of FIG. 8. This figure also illustrates how to establish the mean point between the relationships determined for this repetition for each of the anterior leads, and then how to calculate the square of the residual from the mean point to the relationship determined for each lead (e.g. the square of the variation from the mean);

FIG. 10 represents the graph of FIG. 8 with the mean points for each repetition provided in the graph, with figures provided below.

Figure 11:
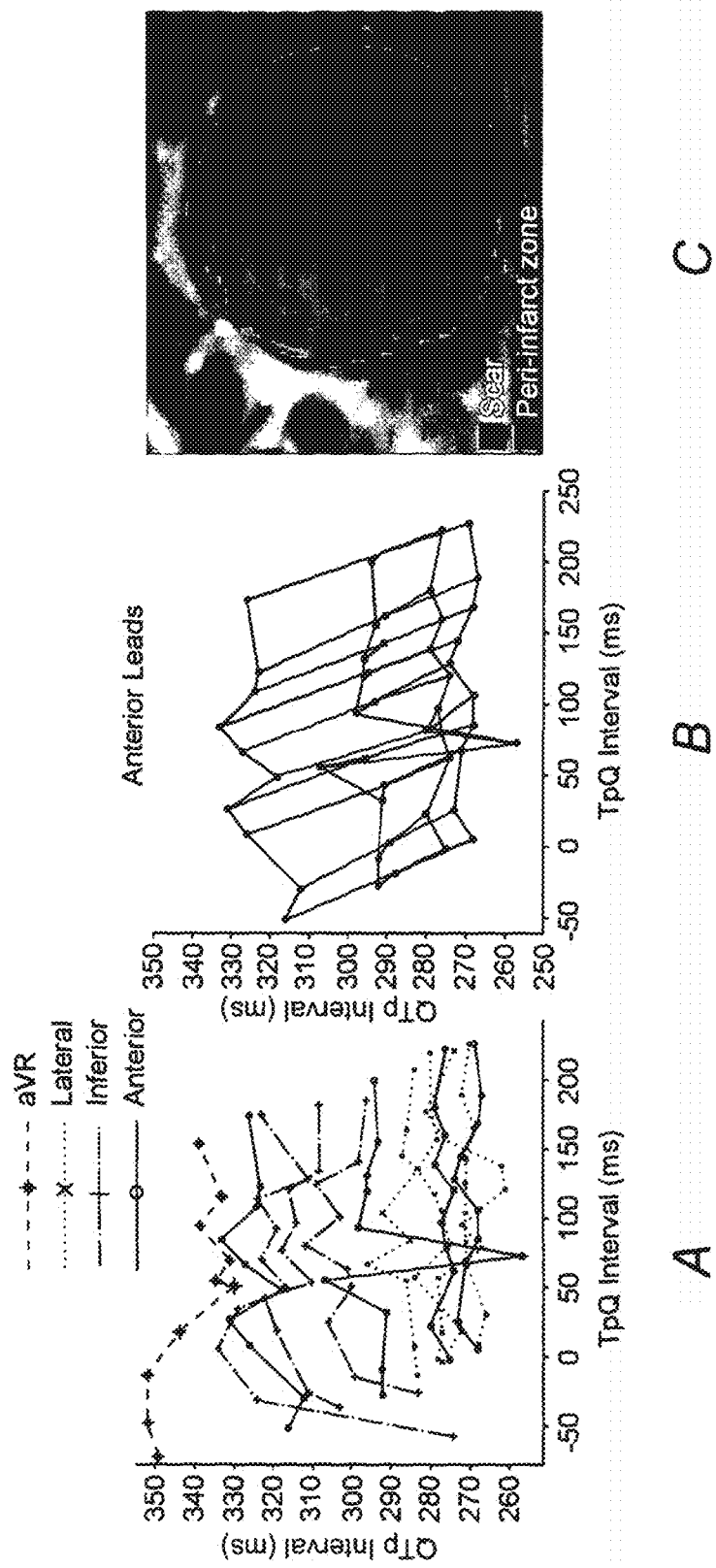

FIG. 11 provides an explanation of the R212 calculation: the graph in A shows the anterior, inferior and lateral leads for a patient who reached the endpoint of ventricular arrhythmia (VA)/death. Each region is analysed separately as seen for the anterior leads in B; the points are grouped by the S1 S2 coupling interval that produced them and the square of the residuals (narrow black lines) from best fit points (black dots) is calculated for each lead at each S1 S2 coupling interval. The mean of these residuals is then taken for each lead. There were differences in the spread of the leads, in particular the lateral leads tended to be more widely spaced than the anterior and inferior leads. A proportion was therefore taken: each lead's value was divided by the population mean value for that lead. The R212 is then taken as the mean of the maximum anterior, inferior and lateral values. The LGE CMR scan for this patient (C) showed a large anteroseptal and apical myocardial infarction with 16% peri-infarct zone (PIZ) anteriorly, 13% inferiorly and 4% laterally corresponding with the R212 components: anterior 3.6, inferior 1.3 and lateral 0.25.

Figure 12:
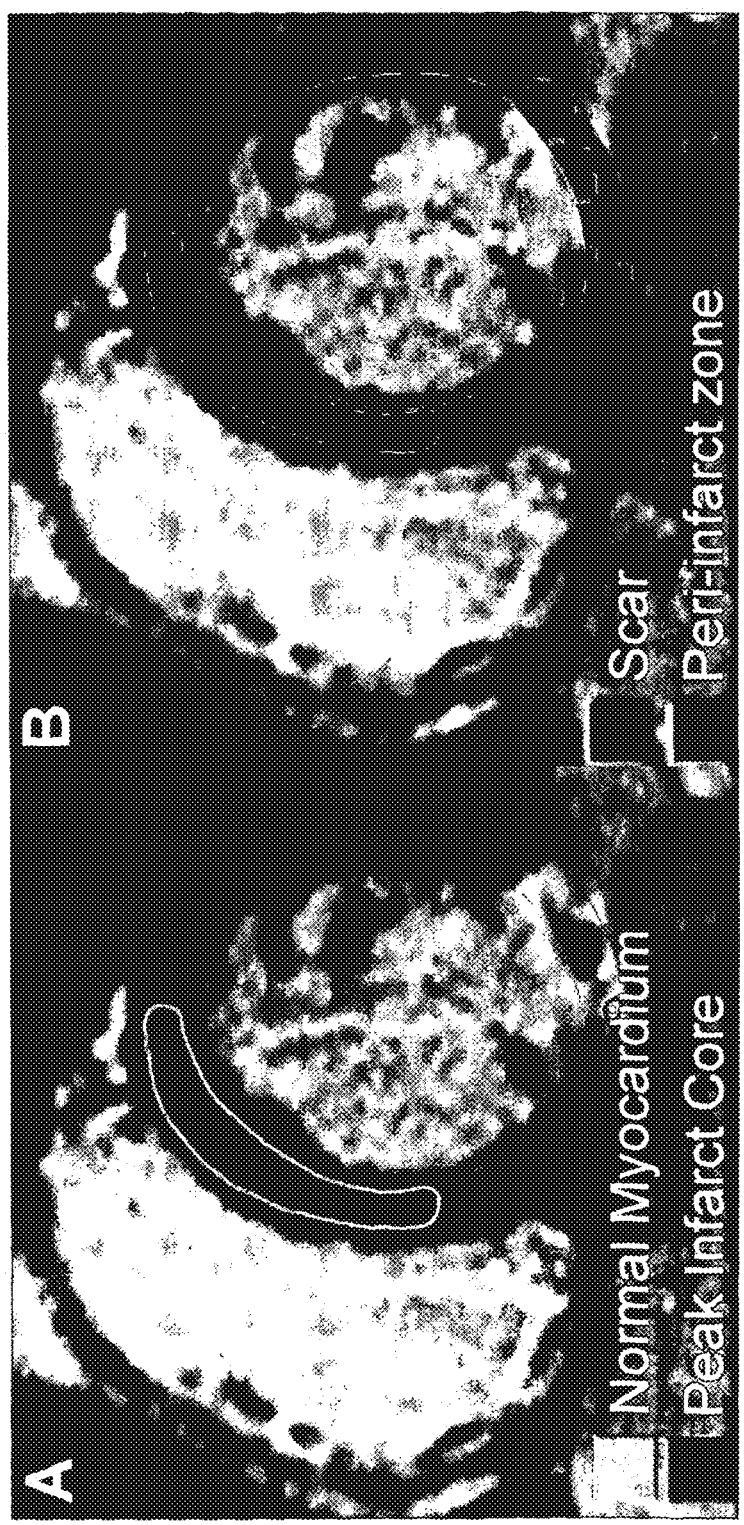

FIG. 12 shows a cardiac magnetic resonance scan. A) First endocardial and epicardial borders are drawn; then a large representative area of "normal myocardium" and a small area of "peak scar" are selected. B) Software analysis identifies all voxels with signal intensity >2 standard deviations (SD) above "normal myocardium" mean intensity and voxels with signal intensity >50% of the "peak scar" are subtracted from this to obtain the PIZ. Identified voxels that are not in the region of an infarct are discarded. The example in B shows an infarct with relatively small PIZ compared with the example in FIG. 11C.

Figure 13:
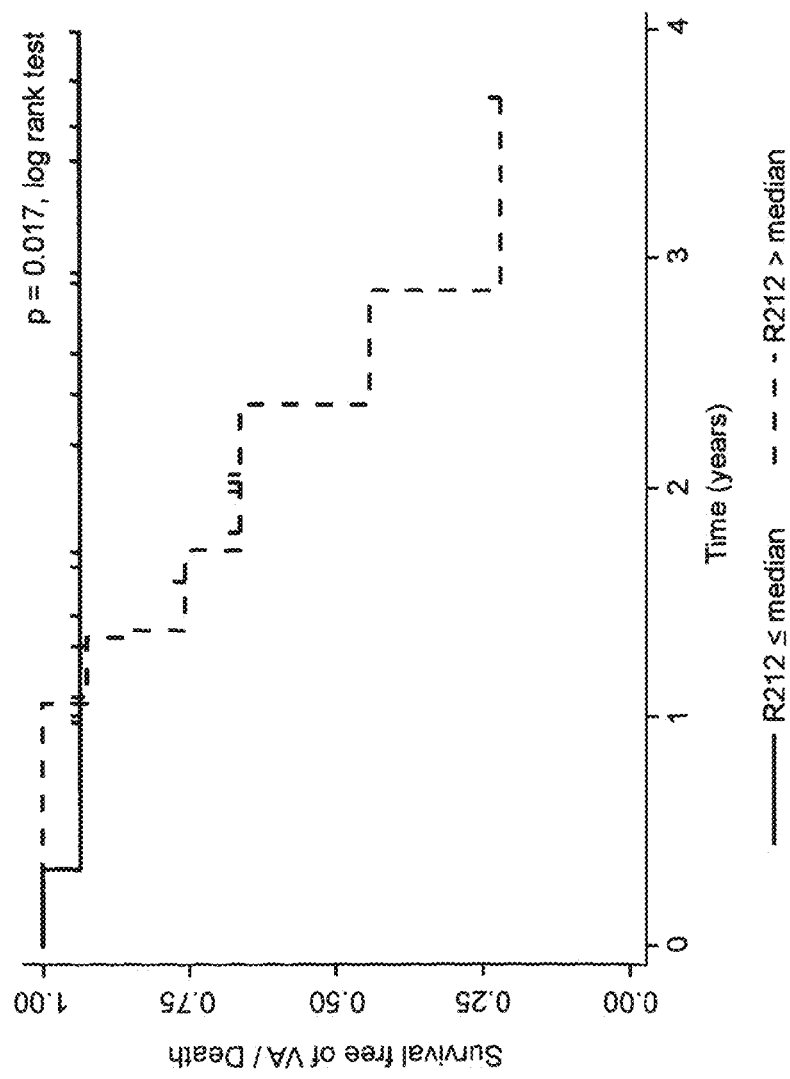

FIG. 13 shows a Kaplan-Meier curve of the probability of survival free of ventricular arrhythmia (VA)/death in the "high risk" group with R212>median and the "low risk" group with R212<=median. The difference in VA/death was significant (p=0.017, log rank test).

Figure 14:
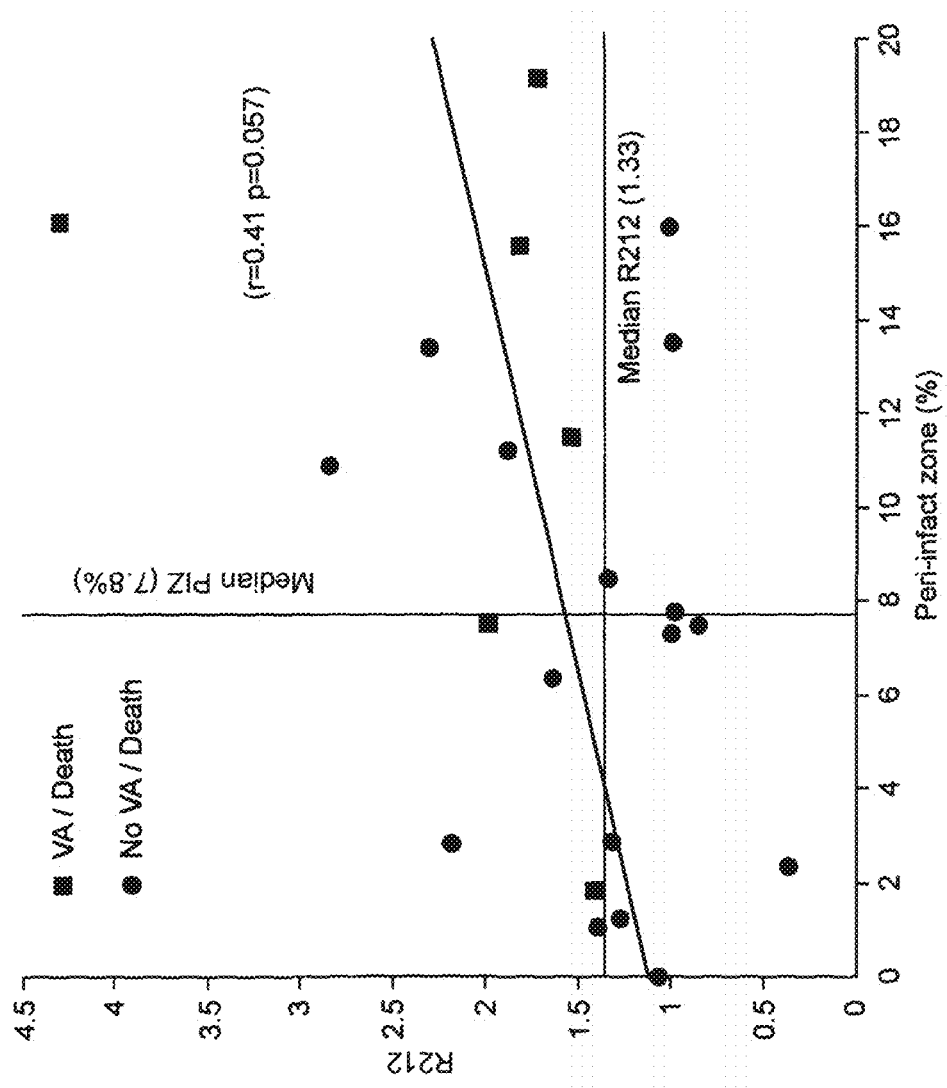

FIG. 14 shows a plot of R212 against PIZ in each of the 22 patients for whom paired data was available. Lines are drawn at the median values for both parameters. A least-squares regression line demonstrates a degree of correlation (r=0.41 p=0.057).

Figure 15:
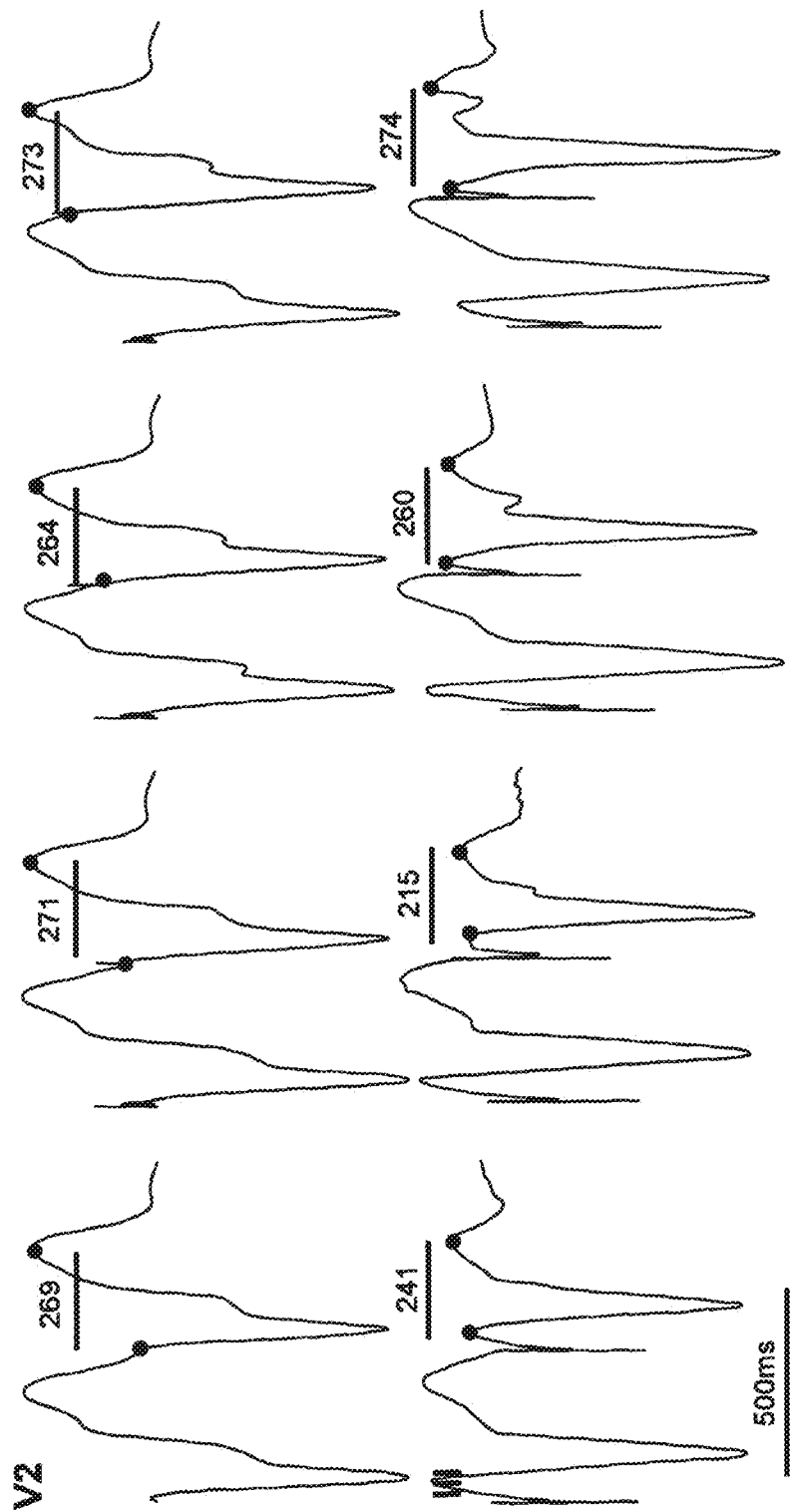

FIG. 15 shows a diagram of the last beat of the drive train and the S1 S2 coupling interval at 400, 380, 360 and 340 ms for leads V2 and III. Demonstration of regional heterogeneity in repolarisation: little change is seen in V2 and the QTp is stable, while lead III is seen to fragment with two peaks and variable QTp. This gross change was seen in 2/4 of the patients who developed VA during follow up.

Figure 16:
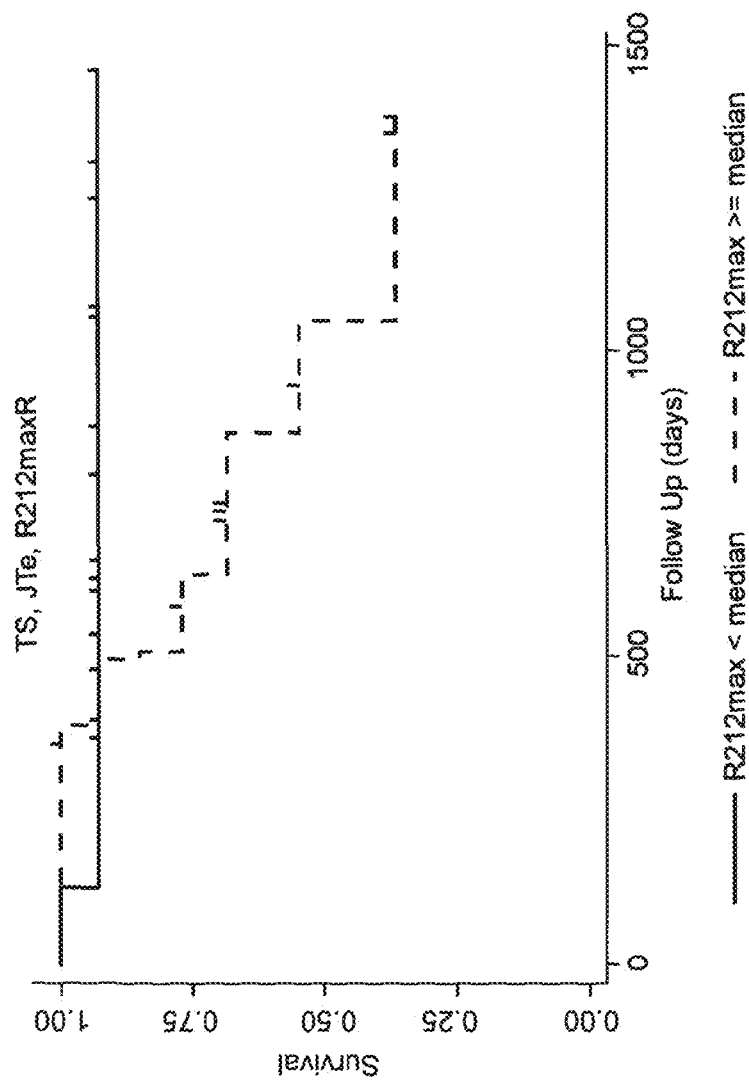

FIG. 16 shows a Kaplan-Meier curve of probability of survival free of VA/death in "high risk" group R212maxR>median and the "low risk" group with R212maxR<=median. The difference in VA/death was significant (P=0.051 log rank test). Here the R212maxR has been calculated using TpS in place of the TpQ and JTe in place of the QTp. Additionally the maximum normalised mean value has been taken rather than the mean of the regional normalised mean maxima.

1. EXAMPLE 1: INCLUSION CRITERIA

Patients being considered for new ICD implantation with NYHA class II-III symptoms of heart failure and documented left ventricular dysfunction.

2. EXAMPLE: EXCLUSION CRITERIA

Unstable coronary heart disease, likely to need percutaneous or surgical intervention Requirement for constant cardiac pacing (such as high grade AV block or for cardiac resynchronisation)

Recent coronary artery bypass graft surgery (within 3 months)

Recent valvular surgery (within 3 months)

Recent myocardial infarction (as documented by appropriate ECG & biochemical analysis) (within 3 months)

2.1 Primary Outcome Measure: ICD Therapy for Ventricular Arrhythmia or Death within a 2 Year Follow Up Period 3. EXAMPLE 3: STUDY PRACTICED ON PATIENTS INCLUDED AFTER ANALYSIS FROM EXAMPLES 1 AND 2

Figure 1A:
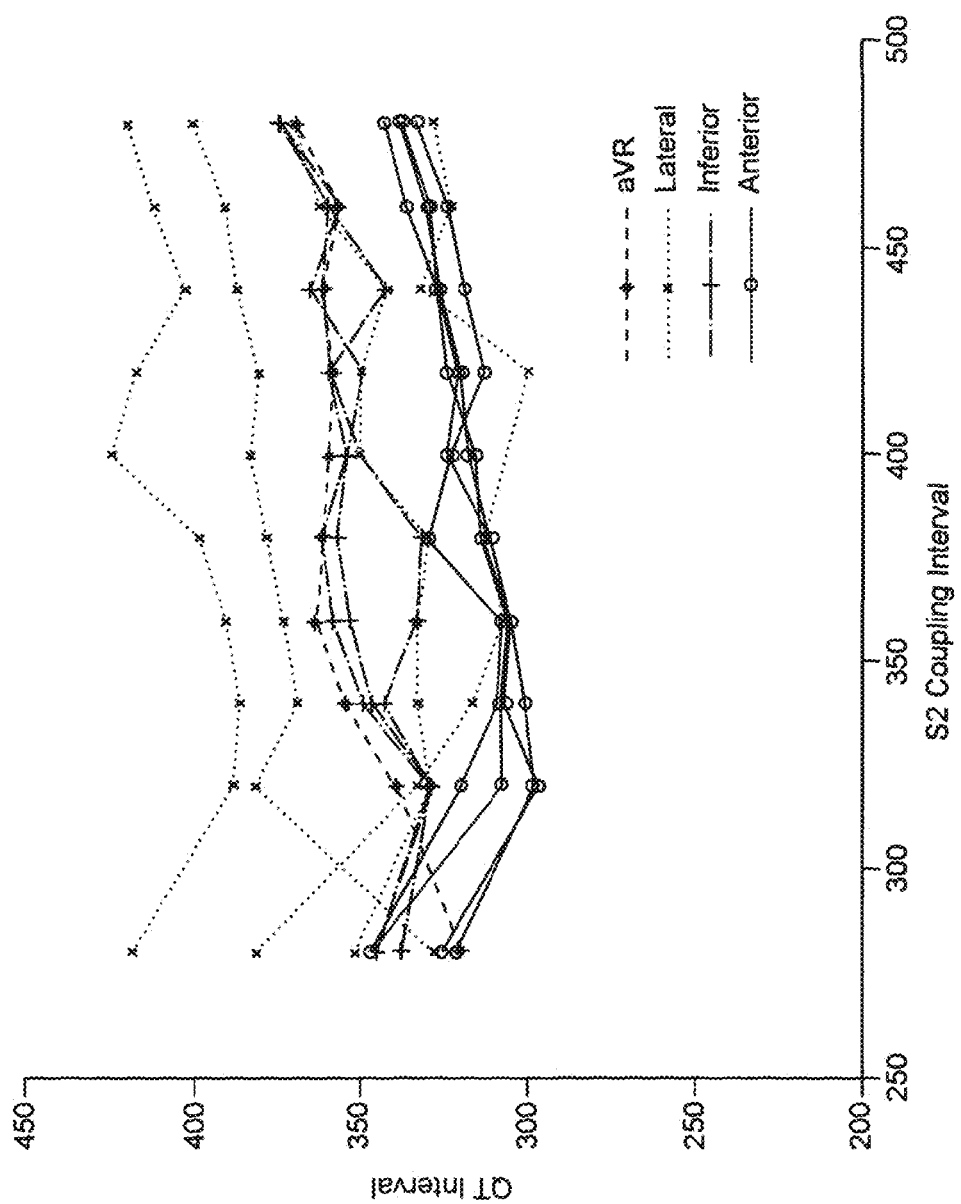
FIG. 1a shows a cutaneous APD restitution graph from a subject suffering from arrhythmia.
Figure 1B:
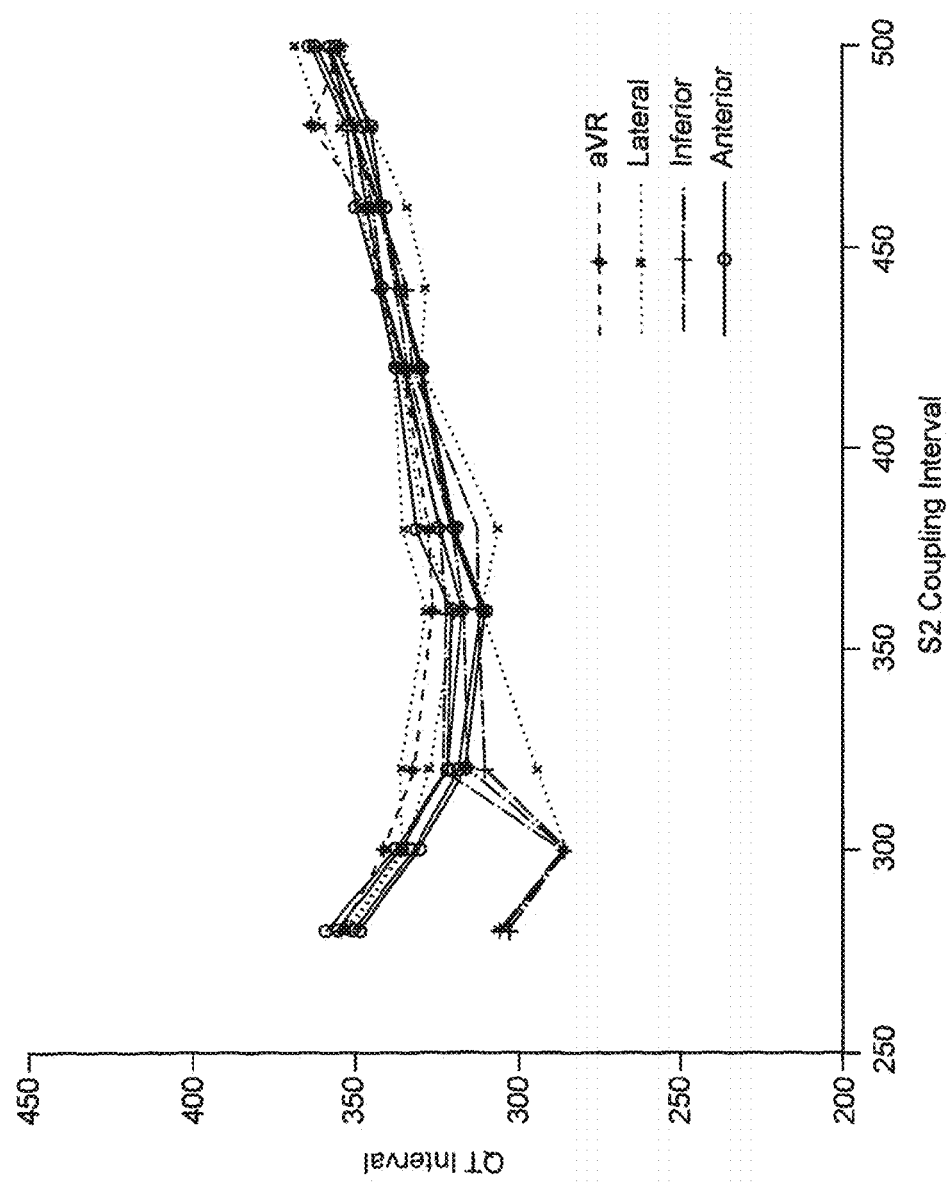
FIG. 1b shows a cutaneous APD restitution graph from a subject that does not suffer from arrhythmia.
Figure 2B:
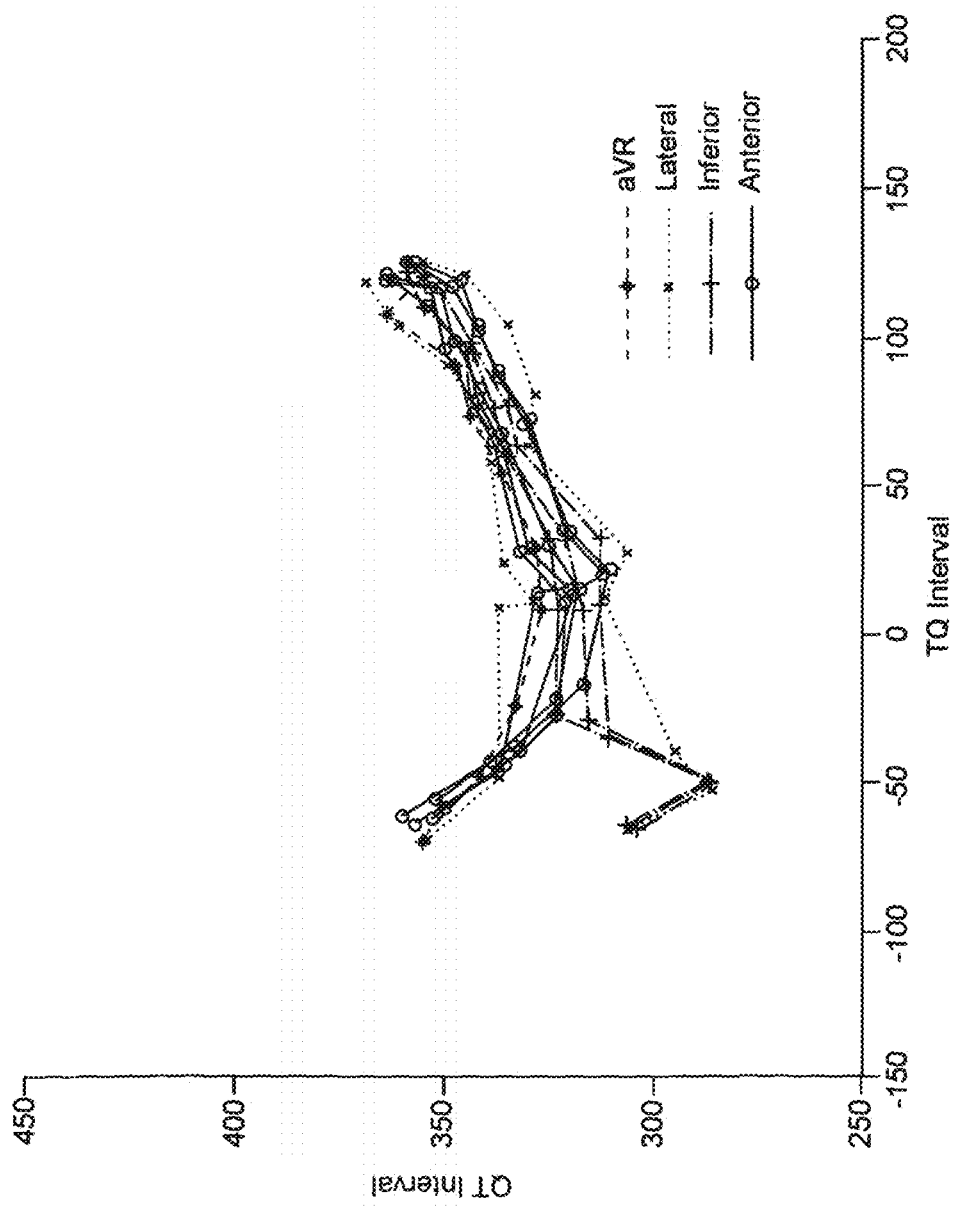
FIG. 2b shows a cutaneous APD restitution graph from a subject that does not suffer from arrhythmia.
Figure 3:
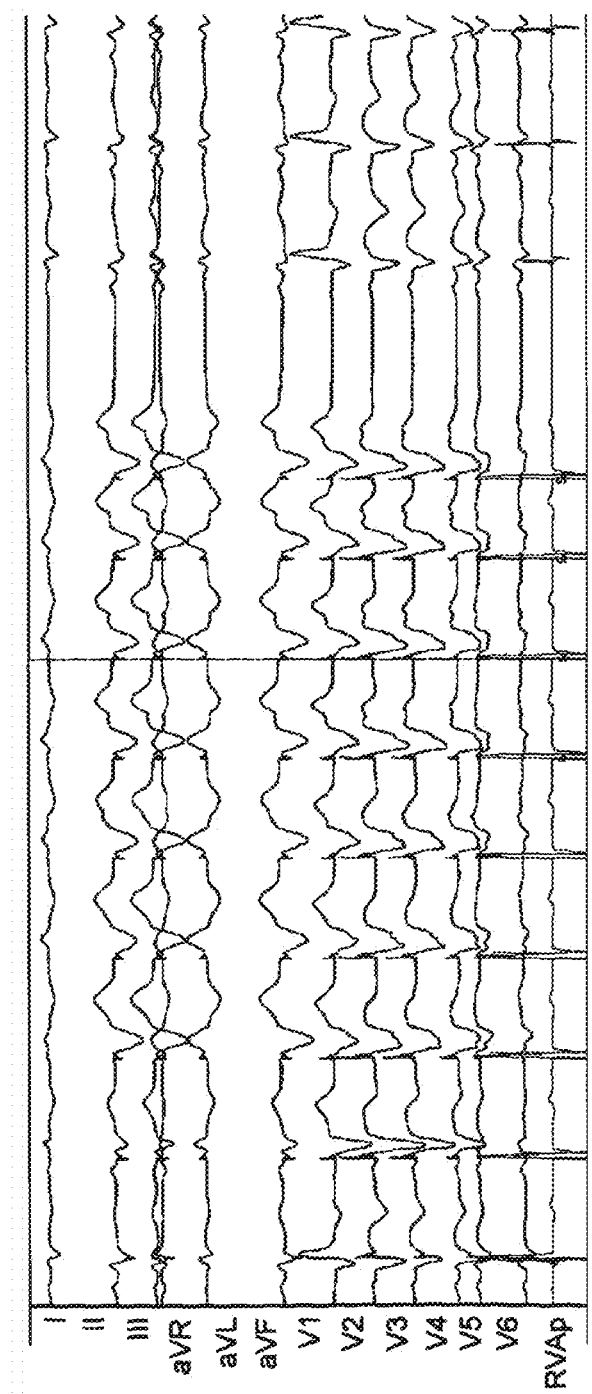
FIG. 3 shows analog digitized and recorded at 1000 Hz with 12-bit resolution data from ECG (expanded from portion of that shown in FIG. 4).
Figure 4:
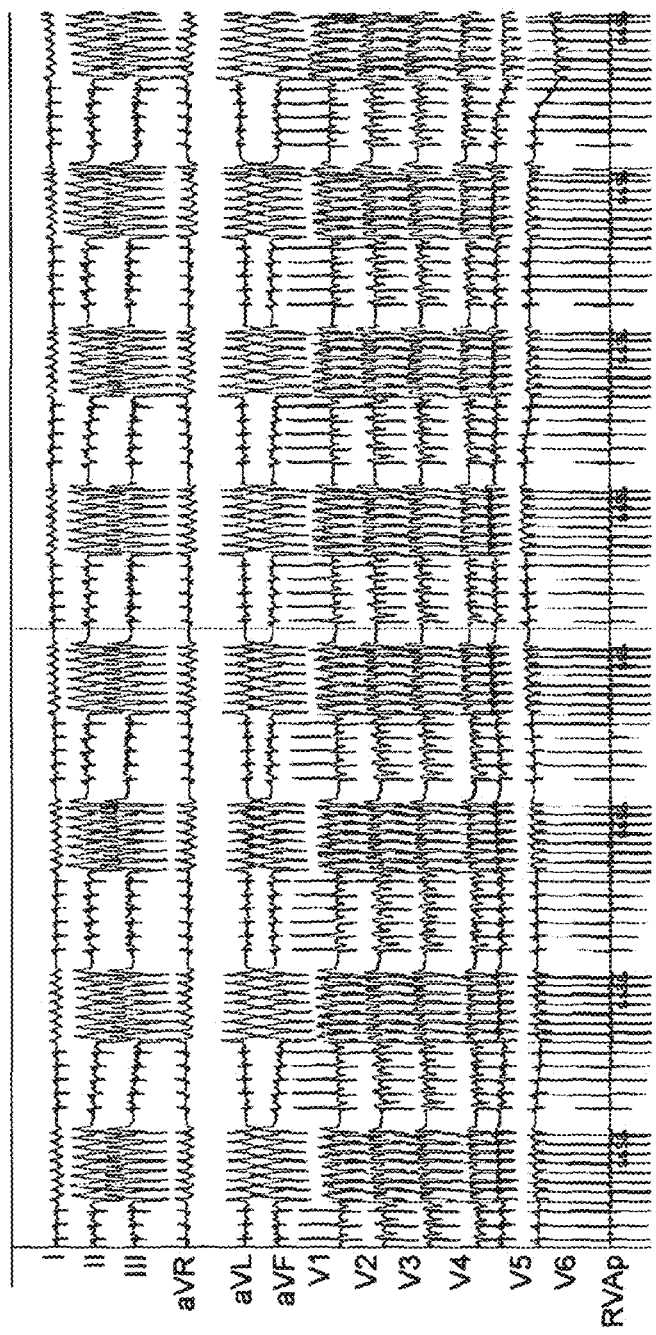
FIG. 4 shows analog digitized and recorded at 1000 Hz with 12-bit resolution data from ECG.

A) Subjects were separated into two groups (the first group being patients determined to at high risk of cardiac arrhythmia; the second group being patients determined to be at low risk of cardiac arrhythmia) studied in the post absorptive state.
B) Appropriate aseptic technique employed throughout.
C) Cutaneous ECG leads were applied in the standard positions and connected to an appropriate electrophysiological recorder. (Bard system used for study standard 12 lead ECG positions)
D) An appropriate transvenous route was selected and the Seldinger technique employed to insert a 6 F venous sheath.
E) An appropriate electrophysiology catheter, for example the 6 F Josephson Quadripolar catheter, was inserted through the sheath.
F) Fluoroscopic guidance was used to manipulate the catheter into the right ventricular apex, where a stable position was obtained.
G) The ventricular stimulation threshold was obtained, preferably via the diastolic approach.
H) An appropriate pacing protocol was delivered with rectangular pulses of 2 ms duration set sufficiently greater than the threshold to achieve reliable stimulation with a preferred value of 3 times the diastolic threshold. The pacing protocol used was the same for each patient in the study.
I) Analog data were digitized and recorded at 1000 Hz with 12-bit resolution, shown in FIGS. 3 and 4. Low pass filter was set to 50 Hz and high pass filter set to 0.01 Hz.
J) Data analysis was performed with custom-written analysis programs in the MATLAB 2009a language.
K) For consistency QT measurements were taken as from the start of the pacing spike to the peak of the T wave and TQ measurements were taken as from the peak of the T wave to the start of the pacing spike.
L) The QT/TQ restitution graphs were determined by plotting QT as a function of preceding TQ and by plotting QT as a function of S2 coupling interval (see FIGS. 1a, 1b, 2a and 2b).

4. EXAMPLE 4: PILOT STUDY EXPLORING THE REGIONAL REPOLARISATION INSTABILITY INDEX IN RELATION TO MYOCARDIAL HETEROGENEITY AND PREDICTION OF VENTRICULAR ARRHYTHMIA AND DEATH 4.1 Methods 4.1.1. Subjects were identified by screening the department audit databases for patients with a history of IHD who had undergone programmed electrical stimulation (PES) between 1 Jan. 2005 and 31 Jul. 2009 as part of clinical risk stratification for ICD implantation and who had had a CMR scan within 6 months of their PES. This identified 43 patients. PES recordings were unavailable for 9 patients and 4 more patients were excluded because only 6 lead ECGs had been recorded. Of the 30 patients whose PES data were available 1 could not be analysed because their drive cycle length (DCL) was changed midway through the protocol. CMR data was then sought for these 30 patients. LGE images were not acquired for 3 patients because of difficulties gating (1) and breath holding (2) and 4 patients could not be analysed because of an incompatibility between the acquisition and peri-infarct zone analysis software. LGE CMR images were available for 23/30 patients.

4.2 Electrophysiological Study 4.2.1. Studies were performed as per the standard departmental protocol which did not change for the duration of the study. Fasting subjects were studied with minimal sedation and with antiarrhythmic drug cessation 4-5 half-lives prior to the procedure. A 6 F Josephson quadripolar catheter was advanced transvenously first to the right ventricular apex (RVA) and then the right ventricular outflow tract (RVOT). Electrocardiograms were recorded using LabSystem Pro (BARD, Lowell) at 1 kHz sampling rate with a low pass filter set to 50 Hz and high pass filter set to 0.01 Hz. The ventricular stimulation test followed a modified Wellens protocol with two 8 beat drive trains at the RVA with drive cycle length (DCL) 600 ms and 400 ms and one 8 beat RVOT drive train with DCL 400 ms. If breakthrough beats were seen in the drive train the DCL was reduced. Up to 3 extrastimuli were used with each drive train; the extrastimulus was typically started at 500/360 ms and reduced in 20 ms steps. Monomorphic VT of duration greater than 30 seconds or associated with haemodynamic compromise was recorded as positive; the test was otherwise recorded as negative. The S1 S2 coupling interval is the period between the last beat of the drive train and the first extrastimulus, this part of the PES was used to derive the R212.

4.3 Analysis of the R212

4.3.1. The electrocardiograms were exported at 16-bit digital resolution for analysis in bespoke software written in MatLab (Mathworks, Natick). The timing of the QRS onset (QRSo) and T wave peak (Tp) were analysed automatically and all data points were manually verified, a senior electrophysiology research fellow blinded to the CMR data, the PES result and endpoint data. The Tp was chosen in preference to the end of the T wave (Te) because of the known difficulties in measuring Te.

Intra and inter-operator reproducibility (8 cardiology specialists mean 10.1 years of cardiology training) were assessed using a representative sample of 48 paced ECG points from the dataset. Mean intra-operator variability for measurement of the QRSo and Tp was 6.3 ms (SD 16.3 ms) vs. inter-operator 6.4 ms (SD 16.7 ms).

4.3.2. Data points were censored according to predetermined rules: 1. Breakthrough beat occurring after beat 6 of the drive train (51/316 drive trains censored), 2. Point indeterminate due to artefact, baseline wander or unclear morphology (256/3089 points censored). For each S1 S2 coupling interval the DI was taken as the period from Tp on the last beat of the DCL to the S2 QRSo as detailed in FIG. 5 and is referred to as the TpQ interval, note the possibility for negative TpQ as measured in this way. The cutaneous surrogate for the APD was taken as the period from S2 QRSo to the S2 Tp (QTp). The TpQ interval and QTp were measured at each S2 performed at the RVA; where possible the DCL 600 ms drive train was used but if it was not present or unusable due to breakthrough beats an alternative DCL was selected.

4.3.3. FIG. 6 shows a representative plot of the dynamic relationship of TQ interval and QT interval for a number of lead types. The focus of the study was on regional electrical heterogeneity and as such the ECG leads were divided into regions based on anterior (V1-4), inferior (II, III, aVF) and lateral (I, aVL, V5, V6) leads. For each lead QTp was plotted as a function of TpQ, points were then grouped by ECG region and S1 S2 coupling interval and for each lead the mean of the squared residuals from best fit points was recorded (FIG. 11). This number was then expressed as a proportion of the mean value for each lead across all patients to account for differences in lead distribution. The mean of the maximum regional values was taken as the R212 and investigated as a marker of VA or death. FIGS. 7 to 10 illustrate further how this analysis is calculated, with Table 3 providing the final analysis of the study shown in FIGS. 7 and 10 where normalised values of the results are calculated.

4.4. Late Gadolinium Enhanced Cardiac Magnetic Resonance Imaging Protocol 4.4.1. Patients underwent LGE CMR as per departmental protocol within 63±63 days of their PES study (in all but one patient the CMR was performed before the PES study) as per the retrospective criteria used to select patients. Comprehensive CMR imaging was performed using a 1.5-T scanner (Siemens Magnetom, Avanto) with ECG triggering and a 6 channel phased array cardiac coil. After scout imaging, steady-state free precession (TrueFISP) cine images were acquired in 4, 3 and 2 chamber-views and a series of short axis slices were obtained using SSFP cine imaging covering the LV from base to apex, with 1 slice every 10 mm. A gadolinium-based contrast agent (0.1-0.2 mmol/kg) was administered intravenously as a bolus and (LGE) images were obtained approximately 10 minutes later with the use of an inversion-recovery, segmented gradient echo sequence.

4.5. CMR Analysis 4.5.1. All analysis was performed offline blinded to patient details using commercially available software. Volumetric analysis was performed by manual tracing of endocardial and epicardial contours; LV end-diastolic volume (LVEDV), end-systolic volume (LVESV), stroke volume (SV), LV ejection fraction (LVEF) and LV end-diastolic mass (LVM) were calculated. LGE images were analysed for scar and PIZ mass using a modification of the Schmidt et al technique. All voxels with signal intensity greater than 50% of peak infarct core were recorded as scar. PIZ was defined as all pixels in the region of the MI with signal intensity >2 standard deviations (SD) above mean intensity in an area of normal myocardium and below 50% of the peak intensity (FIG. 12).

CMR volumes and mass were indexed to height. Scar size is presented as % of LV mass and PIZ as mass in grams, % of LV mass and % of infarct size.

4.6. Statistical Analysis 4.6.1. The primary endpoint was time to VA or death. Parametric data are expressed as mean±standard deviation (SD) and analysed using Student's t-test; non-parametric data as median [inter-quartile range] (IQR) and analysed using Mann-Whitney U test; proportions were analysed using a one sided Fisher's exact test. The population R212 median value was used to separate "high risk" and "low risk" results for the R212 and a Kaplan-Meier survival curve was drawn for R212>median vs. R212≤median with comparison of cumulative VA/death based on logarithmic transformations. Pearson rank correlation was used to look for correlation between the R212 and PIZ. A single Cox proportional hazards model was used to look for independence of the R212>median, PES result, LVEF and QRS duration (QRSD). A p-value <0.05 was considered statistically significant. All analyses were performed using STATA (StataCorp LP, College Station).

4.7. Results 4.7.1. The clinical characteristics, R212 and PIZ data for the 30 patients are summarised in Table 1. R212 data and CMR volumetric analysis, were available for 29 of the patients and LGE CMR data were available for 23, both were available for 22 patients. R212max3 and R212maxRdata for each patient can be found in Table 2. R212max3 being a measurement based on analysis of TpQ and QTp and calculated as the mean of the maximum regional normalised mean values. R212maxR being a measurement based on analysis of TpS and JTe and calculated as the largest normalised mean value. Fourteen patients had a positive PES of whom 13 had ICD implantation, no patients with negative PES had ICD implantation during the study follow up period. Median follow up duration was 725 days (IQR 553 days). Seven patients reached the primary endpoint of VA/death during follow up, 4 VA and 4 deaths (1 patient had successful ICD therapy for VA and subsequently died). Survival was recorded as time to first endpoint/the end of follow up.

4.7.2. When data was analysed using the population median R212max3value, patients with R212>median have a significantly higher VA/death rate than those with R212≤median (6/14 vs. 1/15 p=0.031). Kaplan-Meier survival curves for the 2 groups are shown in FIG. 13, with the populations diverging significantly (p=0.017, log rank test). As would be expected age and PES result were close to being significantly related to outcome but were not correlated with R212. The extent of PIZ showed a trend towards an association with VA/death (13.59, IQR 8.51 vs. 7.51, IQR 8.39, p=0.093) and modest correlation with the R212 (r=0.41 p=0.057), FIG. 14. Cox multivariate analysis of R212 median, PES result, LVEF and QRSD showed that R212 median was an independent predictor of VA/death (p=0.032). Kaplan-Meier survival curves for the same group analysed as R212maxR are shown in FIG. 16.

TABLE 1

| Variable | Whole group (n = 30) | No VA/ Death (n = 23) | VA/ Death (n = 7) | P |
|---|---|---|---|---|
| Age (years) | 67 ± 9 | 65 ± 9 | 72 ± 8 | 0.055 |
| Sex (% male) | 97 | 96 | 100 | ... |
| DCL (ms) | 23 × 600, 1 × 550, 5 × 400 | 16 × 600, 1 × 550, 5 × 400 | All 600 | ... |
| QRSD (ms) | 107 ± 20 | 107 ± 21 | 106 ± 15 | 0.95 |
| LVEF (%) | 31 ± 14 | 32.4 ± 15 | 27 ± 7.5 | 0.34 |
| PES result (positive/total) | 12/30 | 7/23 | 5/7 | 0.068 |
| R2I2 | 1.38 [0.88] | 1.22 [0.90] | 1.76 [0.58] | 0.075 |
| R2I2 > median (positive/total) | 14/29 | 8/22 | 6/7 | 0.031 |

TABLE 1-continued

| Variable | Whole group (n = 30) | No VA/ Death (n = 23) | VA/ Death (n = 7) | P |
|---|---|---|---|---|
| EDV index (ml/cm) | 1.48 ± 0.41 | 1.49 ± 0.41 | 1.45 ± 0.45 | 0.84 |
| SV index (ml/cm) | 0.42 ± 0.14 | 0.43 ± 0.14 | 0.39 ± 0.15 | 0.47 |
| Mass index (gm/cm) | 0.78 ± 0.17 | 0.75 ± 0.23 | 0.77 ± 0.15 | 0.81 |
| Height (cm) | 170 ± 7 | 169 ± 8 | 173 ± 5 | 0.24 |
| Follow up (months) | 24 [18] | 24 [16] | 16 [16] | 0.088 |
| PIZ % | 7.8 [10.7] | 7.5 [8.4] | 13.6 [8.5] | 0.093 |
| PIZ mass (gm) | 10.3 [15.8] | 7.8 [9.7] | 16.7 [12.8] | 0.161 |
| PIZ mass/Scar Mass | 0.67 [0.66] | 0.67 [0.64] | 0.67 [0.53] | 0.78 |
| Scar % | 10.9 [16.5] | 9.67 [13.5] | 21.9 [17.8] | 0.16 |

TABLE 2

| Dead/AT | Time to Death/AT | R2I2max3 | R2I2maxR |
|---|---|---|---|
| 1 | 492 | 1.5713 | 1.3815 |
| 1 | 1046 | 2.0153 | 1.4117 |
| 1 | 122 | 1.1857 | 1.0557 |
| 1 | 384 | 1.436 | 2.3839 |
| 1 | 865 | 1.8388 | 2.4571 |
| 1 | 631 | 1.7603 | 1.208 |
| 1 | 502 | 4.3956 | 2.5317 |
| 0 | 361 | 1.144 | 0.9638 |
| 0 | 601 | 1.0352 | 0.5599 |
| 0 | 1456 | 1.0228 | 1.0991 |
| 0 | 795 | 0.7533 | 0.5867 |
| 0 | 1376 | 1.0829 | 1.2713 |
| 0 | 655 | 2.3692 | 0.9575 |
| 0 | 1247 | 1.0118 | 1.0043 |
| 0 | 578 | 2.2275 | 2.6992 |
| 0 | 874 | 0.379 | 0.6112 |
| 0 | 473 | 3.842 | 4.3457 |
| 0 | 1069 | 0.9167 | 0.8627 |
| 0 | 742 | 1.3929 | 2.6172 |
| 0 | 522 | 1.0024 | 0.324 |
| 0 | 1054 | 1.3069 | 1.1769 |
| 0 | 1306 | 1.3781 | 0.7677 |
| 0 | 732 | 1.6938 | 2.502 |
| 0 | 942 | 0.8577 | 2.4208 |
| 0 | 718 | 1.9053 | 1.9395 |
| 0 | 1350 | 2.9189 | 1.2323 |
| 0 | 354 | 0.5353 | 12.0136 |
| 0 | 391 | 3.3542 | 0.5685 |
| 0 | 624 | 1.2884 | 0.9892 |

TABLE 3

| | Anterior | | | | Lateral | | | | Inferior | | |
|---|---|---|---|---|---|---|---|---|---|---|---|
| | V1 | V2 | V3 | V4 | I | avL | V5 | V6 | II | III | avF |
| Patient x | 749 | 181 | 98 | 111 | 3330 | 1603 | 600 | 1912 | 44 | 58 | 67 |
| Mean Population Mean | 596 | 279 | 357 | 848 | 1440 | 875 | 1383 | 1846 | 180 | 132 | 72 |
| Normalised values for patient x | 1.3 | 0.6 | 0.3 | 0.1 | 2.3 | 1.8 | 0.4 | 1.0 | 0.2 | 0.4 | 0.9 |

4.8. Discussion 4.8.1. This pilot investigation suggests that R212 may be a useful prognostic marker stratifier in patients with IHD at risk of SCD. Patients with ischaemic cardiomyopathy who subsequently had a VA or died had higher R212 than those without an event. The R212 electrical measure of risk shows a moderately strong correlation with an anatomic measure of arrhythmic substrate, the extent of PIZ.

Conceptually the R212 has superficial similarities to QTp dispersion as both involve measurement of inter-lead differences in the QTp interval duration. The R212 has been developed with the weaknesses of QTp dispersion in mind. Firstly it is a dynamic measure: as the S1 S2 coupling interval shortens the complex interplay of restitution and anatomical factors will influence the QRS and T loops, the ECG resulting from this will in part reflect the projection of the changing QRS and T loops but the effects of this are likely to be separate from the changes due to repolarisation heterogeneity. FIG. 15 shows an example of 12 regional differences in repolarisation developing as the S1 S2 coupling interval shortens in a patient who went on to develop VA. Secondly the R212 is based on regional QTp variation and is designed to minimise influence by the baseline QTp dispersion. Thirdly the R212 measurements are made from paced ECGs and the T wave peak has been used for optimal reproducibility.

Abbreviations

| CMR | Cardiac magnetic resonance |
|---|---|
| CV | Conduction velocity |
| DCL | Drive cycle length |
| DI | Diastolic interval |
| ECG | Electrocardiogram |
| EP | Electrophysiological |
| ICD | Implantable cardioverter defibrillator |
| IHD | Ischaemic heart disease |
| IQR | Inter-quartile range |
| JTe | J point to end of the T wave |
| LGE | Late gadolinium enhancement |
| LVEDV | Left ventricular end-diastolic volume |
| LVEF | Left ventricular ejection fraction |
| LVESV | Left ventricular end-systolic volume |
| LVM | Left ventricular end-diastolic mass |
| MI | Myocardial infarction |
| PES | Programmed electrical stimulation |
| PIZ | Peri-infarct-zone |
| QRSo | QRS onset |
| R2I2 | Regional repolarisation instability index |
| RVA | right ventricular apex |
| RVOT | Right ventricular outflow tract |
| SCD | Sudden cardiac death |
| SD | Standard deviation |
| SI | Signal intensity |
| SV | Stroke volume |
| Te | End of the T wave |
| Tp | T wave peak |
| TpS | T wave peak to pacing spike |
| VA | Ventricular arrhythmia |

The invention claimed is:

1. A method for assessing electrical function of a heart, the method comprising:
   a. simultaneously, for each of a plurality of cutaneously-placed electrode leads of an ECG at a first coupling interval of a heart beat, determining a value derived from an output of that lead and which corresponds to an action potential duration;
   b. simultaneously, for each of the plurality of leads of the ECG at the first coupling interval of the heart beat, determining a value derived from an output of that lead and which corresponds to a diastolic interval;
   c. for each of the plurality of leads of the ECG, determining a mathematical relationship between the determined values for action potential duration and for diastolic interval;
   d. quantifying an inter-lead variation by comparing the mathematical relationships for each lead of the plurality of leads as determined in step C; and
   e. assessing the electrical function of the heart based on the quantification of the inter-lead variation such that a greater inter-lead variation is indicative of a greater risk of cardiac arrhythmia, wherein the steps of a. and b. are repeated a plurality of times for a plurality of different coupling intervals.

2. The method as claimed in claim 1, wherein the plurality of leads comprise: limb leads, chest leads, posterior leads, anterior leads, lateral leads, inferior leads, or any combination thereof.

3. The method as claimed in claim 1, wherein there are more than 2 leads.

4. The method as claimed in claim 1, wherein there are 5 or more leads.

5. The method as claimed in claim 1, wherein there are 12 or more leads.

6. The method as claimed in claim 1, wherein quantifying the inter-lead variation comprises quantifying the difference in the gradients of the curves established by plotting the values for (i) action potential duration against diastolic interval or (ii) diastolic interval against action potential duration for each lead on a graph.

7. The method as claimed in claim 1, wherein quantifying the inter-lead variation comprises calculating the standard deviation of the action potential difference from the mean action potential from all leads for each diastolic interval length.

8. The method as claimed in claim 1, wherein quantifying the inter-lead variation comprises quantifying the difference in action potential and/or diastolic interval from the mean action potential and/or diastolic interval for all leads for each coupling interval.

9. The method as claimed in claim 1, wherein:
   I. steps a. to d. are carried out on an output derived from an ECG applied to a first subject to be examined for risk of developing cardiac arrhythmia;
   II. steps a. to d. are carried out on an output derived from an ECG applied to a second subject that has been determined to have normal risk of developing cardiac arrhythmia;
   III. wherein the assessing in step (e) further comprises comparing the inter-lead variation in step d. assessed for the output from the first subject to be examined with the inter-lead variation in step d. assessed for the output from the second subject determined to be at normal risk of developing cardiac arrhythmia; and
   IV. responsive to the inter-lead variation of the first subject being greater than the inter-lead variation of the second subject, determining that the first subject is at increased risk of developing cardiac arrhythmia.

10. The method as claimed in claim 1, wherein:
    I. steps a. to d. are carried out on an output derived from an ECG applied to a subject to be examined for risk of developing cardiac arrhythmia at a first time point;
    II. steps a. to d. are carried out on an output derived from an ECG applied to the same subject at one or more later time point; and
    III. wherein the assessing in step (e) further comprises comparing the inter-lead variation in step d. assessed for the output from the subject to be examined at a first time point with the inter-lead variation in step d. assessed for the output from the subject at one or more later time point; and
    IV. monitoring a progression of heart disease based upon a difference between the inter-lead variation determined in step I and the inter-lead variation determined in step II.

11. The method as claimed in claim 1, wherein the action potential duration is measured as a QT or a JT interval or a QTpeak.

12. A method as claimed in claim 1, wherein the diastolic interval is measured as a TQ interval or a TpeakQ.

13. The method as claimed in claim 1, wherein, when determining the value derived from the output of the leads that correspond to an action potential duration the determination of a beginning and of an end of each action potential duration is consistently determined in the same manner, when determining the value derived from the output of the leads that correspond to a diastolic interval the determination of the beginning and of an end of the diastolic interval is consistently determined in the same manner.

14. The method as claimed in claim 1, wherein the coupling intervals are S1 S2 coupling intervals.

15. A method for determining a subject's need for implantation of an implantable cardioverter defibrillator or the need for administration of an anti-arrhythmic agent, the method comprising:
   a. simultaneously, for each of a plurality of cutaneously-placed electrode leads of an ECG directed to the subject at a first coupling interval of a heart beat, determining a value derived from an output of that lead and which corresponds to an action potential duration;
   b. simultaneously, for each of the plurality of leads of the ECG, directed to the subject at the first coupling interval of the heart beat, determining a value derived from an output of that lead and which corresponds to a diastolic interval;
   c. for each of the plurality of leads of the ECG directed to the subject determining a mathematical relationship between the determined values for action potential duration and for diastolic interval;
   d. quantifying an inter-lead variation by comparing the mathematical relationships for each lead of the plurality of leads as determined in step C; and
   e. assessing the subject's need for the implantation of an implantable cardioverter defibrillator or the administration of an anti-arrhythmic agent based on the quantification of the inter-lead variation such that a greater inter-lead variation is indicative of a greater need for implantation of the implantable cardioverter defibrillator, or administration of an anti-arrhythmic agent, wherein the steps of a. and b. are repeated a plurality of times for a plurality of different coupling intervals.

16. An apparatus for assessing a function of a heart, comprising a computer arranged to receive input from each of a plurality of leads of an ECG and arranged to:
  a. simultaneously, for each of a plurality of cutaneously-placed electrode leads of the ECG at a first coupling interval of a heart beat, determine a value derived from an output of that lead and which corresponds to an action potential duration;
  b. simultaneously, for each of the plurality of leads of the ECG at the first coupling interval of the heart beat, determine a value derived from an output of that lead and which corresponds to a diastolic interval;
  c. for each of the plurality of leads of the ECG, determine a mathematical relationship between the determined values for action potential duration and for diastolic interval;
  d. quantifying an inter-lead variation by comparing the mathematical relationships for each lead of the plurality of leads as determined in step C; and
  e. assess the electrical function of the heart based on the quantification of the inter-lead variation such that a greater inter-lead variation is indicative of a greater risk of cardiac arrhythmia, wherein the steps of a. and b. are repeated a plurality of times for a plurality of different coupling intervals.

17. A non-transitory computer program product when run on a computer arranged to receive input from each of a plurality of leads of an ECG causes the computer to:
  a. simultaneously, for each of a plurality of cutaneously-placed electrode leads of the ECG at a first coupling interval of a heart beat, determine a value derived from an output of that lead and which corresponds to an action potential duration;
  b. simultaneously, for each of the plurality of leads of the ECG at the first coupling interval of the heart beat, determine a value derived from an output of that lead and which corresponds to a diastolic interval;
  c. for each of the plurality of leads of the ECG, determine a mathematical relationship between the determined values for action potential duration and for diastolic interval;
  d. quantify an inter-lead variation by comparing the mathematical relationships for each lead of the plurality of leads as determined in step C; and
  e. assess the electrical function of the heart based on the quantification of the inter-lead variation such that a greater inter-lead variation is indicative of a greater risk of cardiac arrhythmia, wherein the steps of a. and b. are repeated a plurality of times for a plurality of different coupling intervals.

* * * * *